(12) United States Patent
Stewart et al.

(10) Patent No.: US 9,963,611 B2
(45) Date of Patent: May 8, 2018

(54) COMPOSITION FOR USE IN DECREASING THE TRANSMISSION OF HUMAN PATHOGENS

(75) Inventors: Neal G. Stewart, Hong Kong (CN); Francis Chi Nan Lau, Belmont, CA (US); Tai Wai Kung, Hong Kong (CN); Lok Yuen Lo, Hong Kong (CN); Dacey J. Ryan, Hong Kong (CN); Reid W. Von Borstel, Potomac, MD (US)

(73) Assignee: Innonix Technologies, Incorporated, Hong Kong (HK)

( * ) Notice: Subject to any disclaimer, the term of this patent is extended or adjusted under 35 U.S.C. 154(b) by 883 days.

(21) Appl. No.: 13/319,836

(22) PCT Filed: May 21, 2010

(86) PCT No.: PCT/US2010/035864
§ 371 (c)(1),
(2), (4) Date: Nov. 10, 2011

(87) PCT Pub. No.: WO2010/138426
PCT Pub. Date: Dec. 2, 2010

(65) Prior Publication Data
US 2012/0060258 A1    Mar. 15, 2012

Related U.S. Application Data

(60) Provisional application No. 61/298,194, filed on Jan. 25, 2010.

(30) Foreign Application Priority Data
May 29, 2009    (WO) ................ PCT/US2009/045621

(51) Int. Cl.
| | |
|---|---|
| *A41D 13/11* | (2006.01) |
| *C09D 129/04* | (2006.01) |
| *B32B 5/02* | (2006.01) |
| *B32B 5/26* | (2006.01) |
| *A01N 59/16* | (2006.01) |
| *A01N 59/20* | (2006.01) |
| *A62B 23/02* | (2006.01) |
| *C08K 5/092* | (2006.01) |
| *C08K 5/00* | (2006.01) |

(52) U.S. Cl.
CPC ........... *C09D 129/04* (2013.01); *A01N 59/16* (2013.01); *A01N 59/20* (2013.01); *A41D 13/1107* (2013.01); *A41D 13/1192* (2013.01); *B32B 5/022* (2013.01); *B32B 5/26* (2013.01); *A41D 13/11* (2013.01); *A62B 23/025* (2013.01); *B32B 2255/02* (2013.01); *B32B 2255/26* (2013.01); *B32B 2262/0253* (2013.01); *B32B 2307/7145* (2013.01); *B32B 2437/00* (2013.01); *B32B 2535/00* (2013.01); *C08K 5/0058* (2013.01); *C08K 5/092* (2013.01)

(58) Field of Classification Search
None
See application file for complete search history.

(56) References Cited

U.S. PATENT DOCUMENTS

| | | | | |
|---|---|---|---|---|
| 5,467,765 | A  * | 11/1995 | Maturaporn ......... | A62B 23/025 128/206.12 |
| 5,883,026 | A  * | 3/1999 | Reader .................. | A41D 13/11 128/206.12 |
| 2004/0000313 | A1 * | 1/2004 | Gaynor et al. ........... | 128/205.27 |
| 2004/0255946 | A1 | 12/2004 | Gerson et al. | |
| 2006/0198903 | A1 | 9/2006 | Storey et al. | |
| 2007/0281999 | A1 * | 12/2007 | Fox et al. ..................... | 514/557 |
| 2008/0229929 | A1 * | 9/2008 | Marcoon ......................... | 96/296 |
| 2009/0035390 | A1 | 2/2009 | Modak et al. | |

FOREIGN PATENT DOCUMENTS

| | | | | |
|---|---|---|---|---|
| CA | 1295242 | * | 2/1992 | |
| WO | WO0241717 | * | 5/2002 | ............. A41D 13/11 |
| WO | WO2007100654 | * | 9/2007 | ............... C09D 5/00 |
| WO | 2008/009651 A1 | | 1/2008 | |
| WO | 2008/118371 A2 | | 10/2008 | |
| WO | WO2009003057 | * | 12/2008 | ............... B03C 3/00 |

* cited by examiner

*Primary Examiner* — Bethany P Barham
*Assistant Examiner* — Ping Cao
(74) *Attorney, Agent, or Firm* — Trojan Law Offices

(57) ABSTRACT

A composition for coating a polypropylene-based fabric or polypropylene-based material for use in decreasing the transmission of human pathogens. A device such as a protective face mask made from a polypropylene-based fabric or polypropylene-based material coated with the composition.

6 Claims, 11 Drawing Sheets

COMPOSITION FOR USE IN DECREASING THE TRANSMISSION OF HUMAN PATHOGENS

CROSS-REFERENCE TO RELATED APPLICATIONS

The present Application is a U.S. National Stage Application under 35 U.S.C. § 371 of International Patent Application No. PCT/US2010/035864, filed on May 21, 2010, which claims priority from International Patent Application No. PCT/US09/45621 filed May 29, 2009 and titled "Protective Face Mask"; and claims the benefit of U.S. Provisional Patent Application No. 61/298,194 filed Jan. 25, 2010 and titled "Composition for Decreasing the Hydrophobicity of Polypropylene"; the contents of which are incorporated in this disclosure by reference in their entirety.

BACKGROUND

There are a variety of infectious human diseases, such as human respiratory tract infections, that are caused by human pathogens such as bacteria, fungi and viruses. For example, viral causes of infectious human diseases (and their associated diseases) include: Influenza A virus (including 'swine flu' such as the 2009 H1N1 strain); Influenza B-C virus (coryza; 'common cold'); Human adenovirus A-C (various respiratory tract infections; pneumonia); Human Para-influenza virus (coryza; 'common cold;' croup); Mumps virus (epidemic parotitis); Rubeola virus (measles); Rubella virus (German measles); Human respiratory syncytial virus (RSV) (coryza; 'common cold'); Human *coronavirus* (SARS virus) (SARS); Human *rhinovirus* A-B (coryza; 'common cold'); *parvovirus* B19 (fifth disease); *variola virus* (smallpox); *varicella-zoster virus* (herpes virus) (chickenpox); Human *enterovirus* (coryza; 'common cold'); *Bordetella pertussis* (whooping cough); *Neisseria meningitidis* (meningitis); *Corynebacterium diphtheriae* (diphtheria); *Mycoplasma pneumoniae* (pneumonia); *Mycobacterium tuberculosis* (tuberculosis); *Streptococcus pyogenes/pneumoniae* (strep throat, meningitis, pneumonia); and *Haemophilus influenzae* Type B (epiglottis, meningitis, pneumonia).

Many of the human respiratory tract infections result in significant morbidity and mortality. For example, seasonal epidemics of influenza viruses worldwide infect an estimated 3 million to 5 million people, and kill between 250,000 to 500,000 people each year. In addition, cyclical influenza virus pandemics occur, such as the influenza outbreak in 1918 which killed between 20 million and 50 million people worldwide.

Among the modes of transmission of these infectious human diseases are by airborne transmission of infectious particles expelled from the respiratory tract of an infected person by coughing or sneezing, or by simple exhalation, and into the gastrointestinal or respiratory systems of a previously non-infected person by inhalation. To combat this form of transmission, facial masks have been developed that either mechanically intercept the infectious particles, or that inactivate the infectious particles, or both mechanically intercept the infectious particles and inactivate the infectious particles, by a variety of mechanisms.

Protective facial masks are designed to be worn by both the infected person to prevent transmission of infection, and by the non-infected person to prevent being infected. In order to keep the costs of production reasonable, facial masks generally are produced in only a few sizes or only one size. The problem with using conventional facial masks produced in a few sizes or only one size, however, is that the facial masks tend not to fit a substantial portion of the human population sufficiently tight around the face, and in particular around the nose of the wearer to prevent near complete ingress or egress of the airborne infectious particles. To address this deficiency, facial masks have been designed to incorporate mechanical structures, such as elastic bands that loop around the ears to seal the facial mask against the face of the wearer by increasing the force that holds the facial mask in place, thereby deforming the perimeter of the facial mask to more tightly fit the face of the wearer. While mitigating the problem, these mechanical structures create an unpleasant sensation of pressure for the wearer over time, and tend to limit the period that the facial mask can be worn. This is especially true for children who have a lower tolerance of discomfort. Additionally, conventional facial masks do not inactivate a substantial portion of the infectious particles that ingress between the facial mask and the face of the wearer.

Therefore, there is a need for a new protective facial mask that addresses these problems.

SUMMARY

According to one embodiment of the present invention, there is provided a composition for coating a polypropylene-based fabric or polypropylene-based material, such as for example a fabric or a material for use in decreasing the transmission of human pathogens. The composition comprises an aqueous solution of citric acid, polyvinyl alcohol and one or more than one nonionic surfactant. In one embodiment, the polyvinyl alcohol is partially hydrolyzed. In another embodiment, the composition comprises between 0.5% to 4% citric acid and between 0.5% and 4% polyvinyl alcohol. In another embodiment, the composition comprises between 1% to 3% citric acid and between 1% and 3% polyvinyl alcohol. In one embodiment, the nonionic surfactant is polyoxyethylene (20) sorbitan. In one embodiment, the composition comprises between 0.1% and 1% of the nonionic surfactant. In one embodiment, the composition comprises between 0.2% and 0.7% of the nonionic surfactant. In another embodiment, the composition comprises 2% polyvinyl alcohol, 2% citric acid and 0.5% of the nonionic surfactant. In one embodiment, the composition further comprises one or more than one type of bactericidal, fungicidal or viricidal agent. In one embodiment, the agent is a multivalent metallic ion. In another embodiment, the agent is a divalent metallic salt. In another embodiment, the agent is selected from the group consisting of copper acetate, copper oxide, copper sulfate and zinc acetate. In one embodiment, the composition comprises between 0.5% and 5% of each of the one or more than one metallic ion. In another embodiment, the composition comprises between 1% and 4% of each of the one or more than one metallic ion. In another embodiment, the composition comprises 3% of each of the one or more than one metallic ion. In one embodiment, the composition comprises 2% citric acid, 2% polyvinyl alcohol, 0.5% polyoxyethylene (20) sorbitan, 3% copper acetate and 3% zinc acetate.

According to another embodiment of the present invention, there is provided a polypropylene-based fabric coated with a composition according to the present invention. According to another embodiment of the present invention, there is provided a polypropylene-based material comprising a plurality of layers, where one or more than one of the plurality of layers comprises a polypropylene-based fabric according to the present invention.

According to another embodiment of the present invention, there is provided a device that decreases the transmission of one or more than one human pathogen by antibacterial, antifungal and antiviral activity. The device comprises a polypropylene-based fabric or a polypropylene-based material according to the present invention.

According to another embodiment of the present invention, there is provided a facial mask that decreases the transmission of one or more than one human pathogen by antibacterial, antifungal and antiviral activity. The facial mask comprises a polypropylene-based fabric or a polypropylene-based material according to the present invention. In one embodiment, the facial mask further comprises one or more than one reactive dye.

According to another embodiment of the present invention, there is provided a facial mask that decreases the transmission of one or more than one human pathogen by antibacterial, antifungal and antiviral activity. The facial mask comprises a polypropylene-based material comprising four layers, Layer #1, Layer #2, Layer #3 and Layer #4 oriented from the front surface to the back surface; where Layer #1 comprises spunbond nonwoven polypropylene fiber having a density of 45 g/m$^2$ and coated with a composition comprising 2% citric acid, 2% polyvinyl alcohol and 0.5% polyoxyethylene (20) sorbitan, Layer #2 comprises spunbond nonwoven polypropylene fiber having a density of 45 g/m$^2$ and coated with a composition comprising 2% citric acid, 2% polyvinyl alcohol, 0.5% polyoxyethylene (20) sorbitan, 3% copper acetate and 3% zinc acetate, Layer #3 comprises melt-blown polypropylene fiber having a density of 18 g/m$^2$, and Layer #4 comprises spunbond nonwoven polypropylene fiber having a density of 25 g/m$^2$.

According to another embodiment of the present invention, there is provided a facial mask for decreasing the transmission of one or more than one human pathogen to and from a human wearer of the facial mask. The facial mask comprises a) a body comprising a front surface of the body, an opposing back surface of the body, and a perimeter of the body defining a shape of the body; and b) a flap attached to the body at a body-flap junction; the flap comprising a front surface of the flap, an opposing back surface of the flap, and a perimeter of the flap defining a shape of the flap; where the body and the flap comprise a polypropylene-based material comprising four layers, Layer #1, Layer #2, Layer #3 and Layer #4 oriented from the front surface to the back surface; and where Layer #1 comprises spunbond nonwoven polypropylene fiber having a density of 45 g/m$^2$ and coated with a composition comprising 2% citric acid, 2% polyvinyl alcohol and 0.5% polyoxyethylene (20) sorbitan, Layer #2 comprises spunbond nonwoven polypropylene fiber having a density of 45 g/m$^2$ and coated with a composition comprising 2% citric acid, 2% polyvinyl alcohol, 0.5% polyoxyethylene (20) sorbitan, 3% copper acetate and 3% zinc acetate, Layer #3 comprises melt-blown polypropylene fiber having a density of 18 g/m$^2$, and Layer #4 comprises spunbond nonwoven polypropylene fiber having a density of 25 g/m$^2$.

According to another embodiment of the present invention, there is provided a facial mask for decreasing the transmission of one or more than one human pathogen to and from a human wearer of the facial mask. The facial mask comprises a) a body comprising a front surface of the body, an opposing back surface of the body, and a perimeter of the body defining a shape of the body, and a central seam; b) a flap attached to the body at a body-flap junction; the flap comprising a front surface of the flap, an opposing back surface of the flap, and a perimeter of the flap defining a shape of the flap; c) a resilient member attached to the back surface of the flap; d) a deformable strip attached to the body; and e) one or more than one extension attached to the body for securing the facial mask to the head of a wearer; where the perimeter of the body comprises a right lateral edge, a left lateral edge connected to the right lateral edge at a bottom junction of the perimeter, and a top edge connecting the right lateral edge to the left lateral edge; where the perimeter of the flap comprises in continuity, a right vertical side, a right arcuate side, a central curved region, a left arcuate side, a left vertical side, and a base partially forming the body-flap junction and connecting the right vertical side to the left vertical side; where the shape of the flap is an inverted U-shape when looking at the front surface of the body or the back surface of the body with the bottom junction oriented down; where both the body and the flap comprise a material comprising four layers, Layer #1, Layer #2, Layer #3 and Layer #4 oriented from the front surface to the back surface; and where Layer #1 comprises spunbond nonwoven polypropylene fiber having a density of 45 g/m$^2$ and coated with a composition comprising 2% citric acid, 2% polyvinyl alcohol and 0.5% polyoxyethylene (20) sorbitan, Layer #2 comprises spunbond nonwoven polypropylene fiber having a density of 45 g/m$^2$ and coated with a composition comprising 2% citric acid, 2% polyvinyl alcohol, 0.5% polyoxyethylene (20) sorbitan, 3% copper acetate and 3% zinc acetate, Layer #3 comprises melt-blown polypropylene fiber having a density of 18 g/m$^2$, and Layer #4 comprises spunbond nonwoven polypropylene fiber having a density of 25 g/m$^2$.

According to another embodiment of the present invention, there is provided a method of decreasing the transmission of one or more than one human pathogen. The method comprises a) providing a facial mask according to the present invention; and b) wearing the facial mask.

FIGURES

These and other features, aspects and advantages of the present invention will become better understood with regard to the following description, appended claims, and accompanying figures where:

DESCRIPTION

Figure 1:
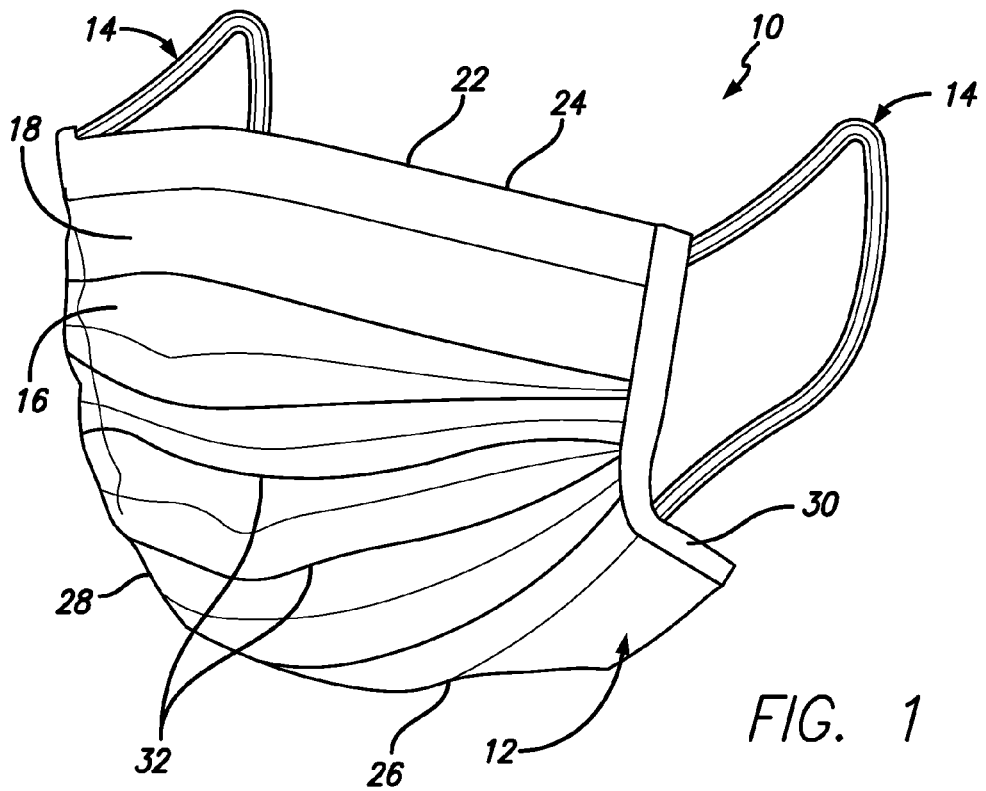
FIG. 1 is a frontal perspective view of one type of conventional facial mask.

According to one embodiment of the present invention, there is provided a composition for coating a polypropylene-based fabric or polypropylene-based material, such as for example a fabric or a material for use in decreasing the transmission of the human pathogens. The composition comprises an aqueous solution of citric acid, polyvinyl alcohol and one or more than one nonionic surfactant. In one embodiment, the composition further comprises one or more than one type of bactericidal, fungicidal or viricidal agent, such as for example an agent selected from the group consisting of copper acetate, copper oxide, copper sulfate and zinc acetate. According to another embodiment of the present invention, there is provided a polypropylene-based fabric coated with a composition according to the present invention. According to another embodiment of the present invention, there is provided a polypropylene-based material comprising a plurality of layers, where one or more than one of the plurality of layers comprises a polypropylene-based fabric according to the present invention. According to another embodiment of the present invention, there is provided a device that decreases the transmission of one or more than one human pathogen by antibacterial, antifungal and antiviral activity. The device comprises a polypropylene-based fabric or a polypropylene-based material according to the present invention. According to another embodiment of the present invention, there is provided a facial mask that decreases the transmission of one or more than one human pathogen by antibacterial, antifungal and antiviral activity. The facial mask comprises a polypropylene-based fabric or a polypropylene-based material according to the present invention. In one embodiment, the facial mask further comprises one or more than one reactive dye. According to another embodiment of the present invention, there is provided a method of decreasing the transmission of one or more than one human pathogen. The method comprises a) providing a facial mask according to the present invention; and b) wearing the facial mask. The composition, fabric, material, device and method will now be disclosed in more detail.

As used in this disclosure, except where the context requires otherwise, the term "comprise" and variations of the term, such as "comprising," "comprises" and "comprised" are not intended to exclude other additives, components, integers or steps.

All dimensions specified in this disclosure are by way of example of one or more than one embodiment of the present invention only and are not intended to be limiting. As will be understood by those with skill in the art with reference to this disclosure, the actual dimensions of any device or part of a device disclosed in this disclosure will be determined by its intended use.

As used in this disclosure, "human pathogen" comprises bacteria, fungi and viruses, or other microorganisms that cause human diseases, including bacteria, fungi and viruses or other microorganisms that cause human respiratory tract infections.

As used in this disclosure, "flap" means a piece of the facial mask that when folded over at the body-flap junction toward the back surface of the body of the facial mask, inverts the layers of the material of the flap with respect to the layers of material of the body. Therefore, a pleat in a conventional facial mask is not a "flap" within the meaning of the present disclosure, because no such inversion of the layers of the material occur no matter how the pleats are opened or closed during use of the conventional facial mask.

As used in this disclosure, a material comprises a plurality of layers, such as a layer of fabric according to the present invention.

As used in this disclosure, "resilient member" means a substrate that readily regains its original shape after compression, where the resilient member has a first thickness before the application of a compressive force, a second thickness after the application of the compressive force, and a third thickness after the cessation of the application of the compressive force, where second thickness is 75% or less of the first thickness, and where the third thickness is between 90% and 100% of the first thickness, where the thicknesses can be measured at any location across the substrate.

As used in this disclosure, "binding substance" means a chemical group that chemically binds a human pathogen, rather than presenting only a physical barrier to spatial passage of the human pathogen. Similarly, "bind," and its related terms such as "binds," "binding" and "binding action," refer to a chemical process, not merely the presentation of only a physical barrier to the spatial passage of the human pathogen.

As used in this disclosure, "cellulosic" means "comprising cellulose."

As used in this disclosure, all amounts of substances are given in weight of the substance as a percent of total weight, unless otherwise specified. For example, "an aqueous solution of between 0.5% and 4% polyvinyl alcohol . . . " means '100 grams of aqueous solution contains between 0.5 grams of polyvinyl alcohol and 4 grams of polyvinyl alcohol . . . '

Figure 2:
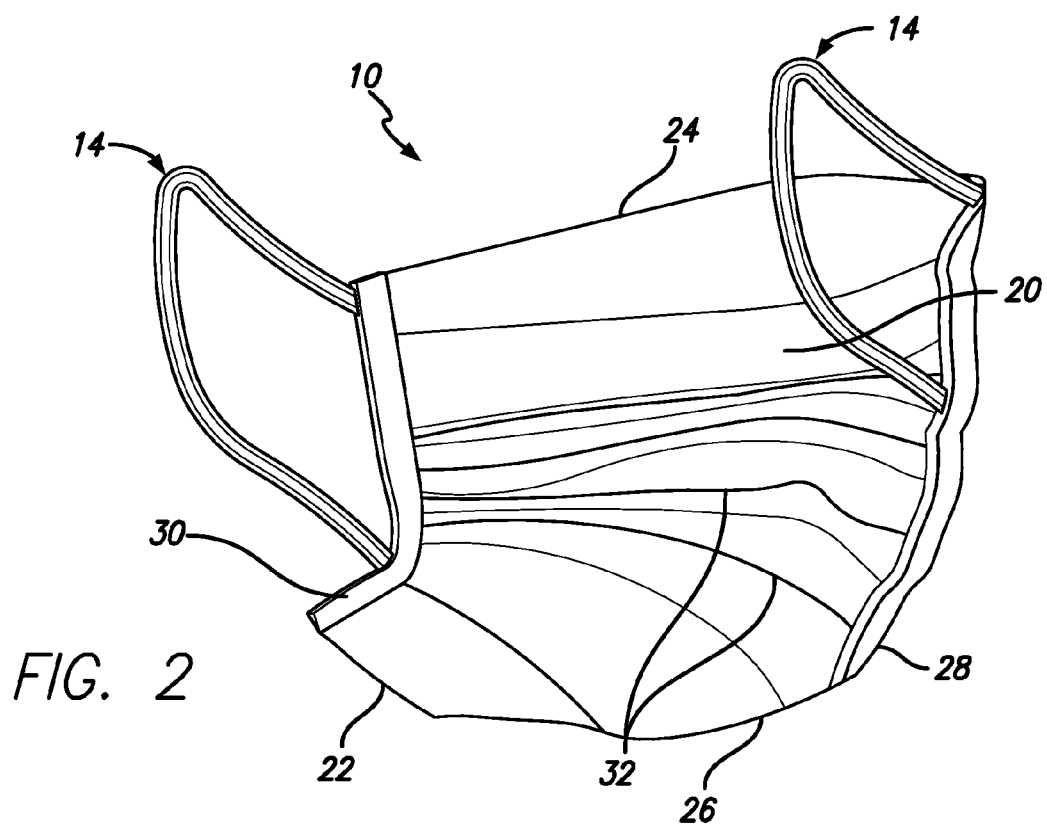
FIG. 2 is a back perspective view of the conventional facial mask shown in FIG. 1.

Referring now to FIG. 1 and FIG. 2, there are shown, respectively, a frontal perspective view of one type of conventional facial mask (FIG. 1); and a back perspective view of the facial mask shown in FIG. 1 (FIG. 2). As can be seen, the conventional facial mask 10 comprises a body 12 for covering the mouth and nose of a human wearer, and further comprises one or more than one extension 14 joined to the body 12 for securing the facial mask 10 to the head of the wearer. The body 12 comprises a material 16 having a front surface 18 and an opposing back surface 20. The body 12 further comprises a perimeter 22 comprising a top edge 24, a bottom edge 26, and two lateral edges 28, 30 each connecting the top edge 24 with the bottom edge 26. The body 12 further comprises a plurality of pleats 32, each pleat extending from one lateral edge 28 to the other lateral edge 30, the pleats 32 allowing expansion of the body 12 centrally thereby forming a convex shape toward the front surface 18 of the body 12 when expanded, in order to more closely approximate the facial curves of a wearer of the facial mask 10.

Figure 3:
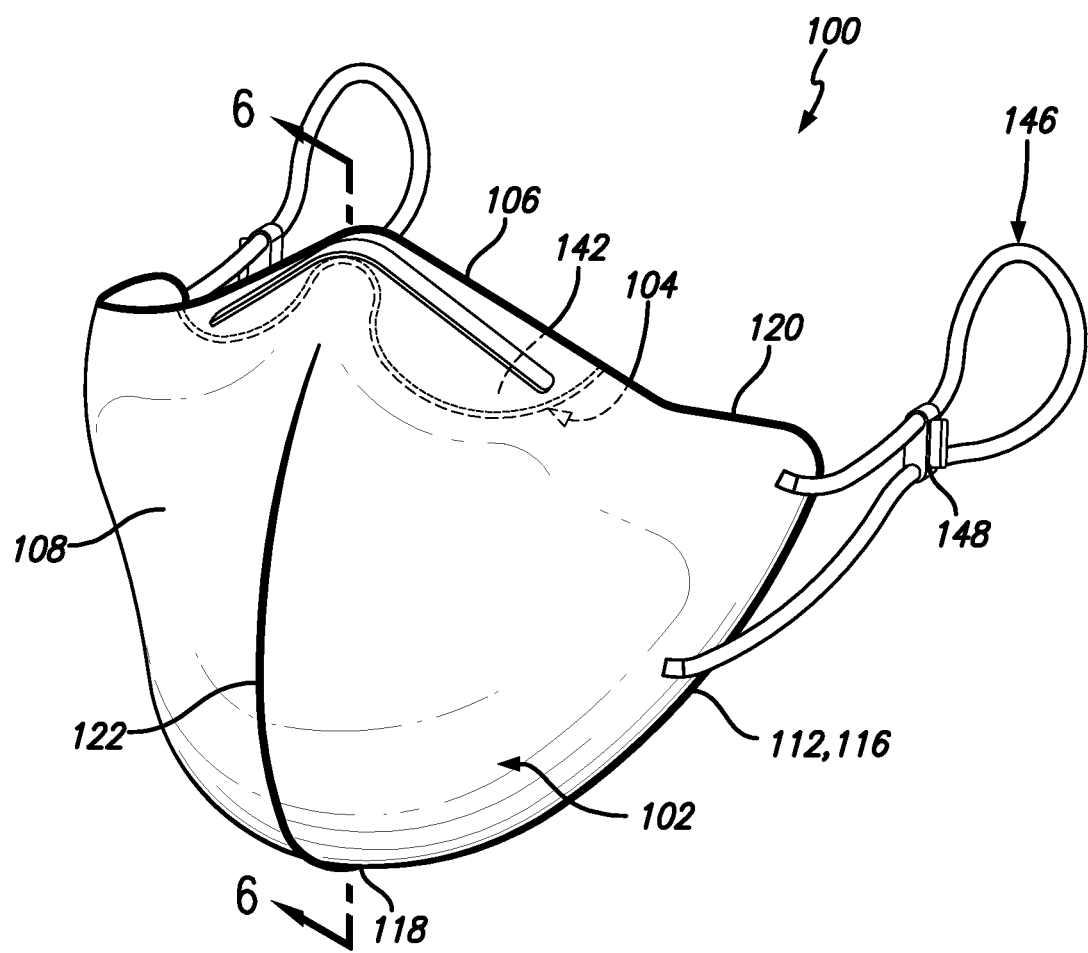
FIG. 3 is a frontal perspective view of one embodiment of a facial mask according to the present invention.
Figure 4:
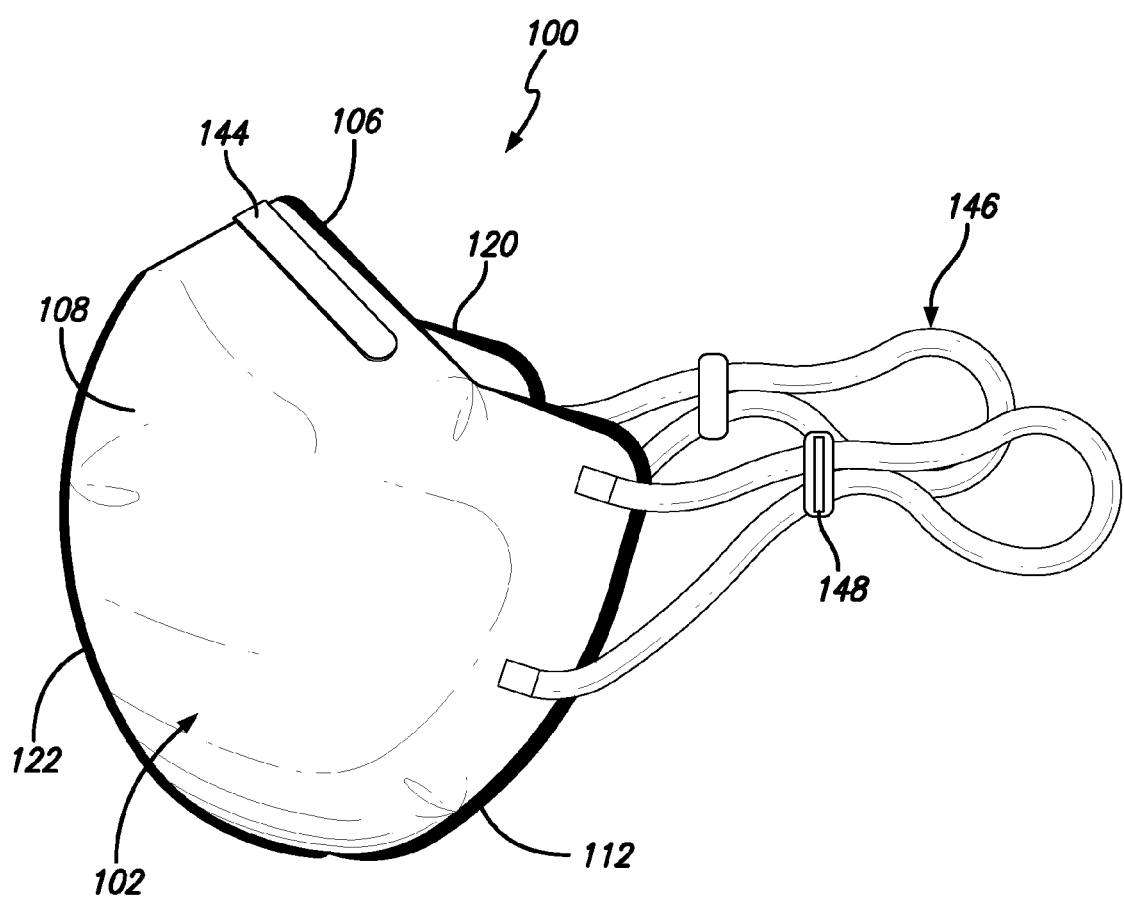
FIG. 4 is a frontal-lateral perspective view of the embodiment of the facial mask shown in FIG. 3.
Figure 5:
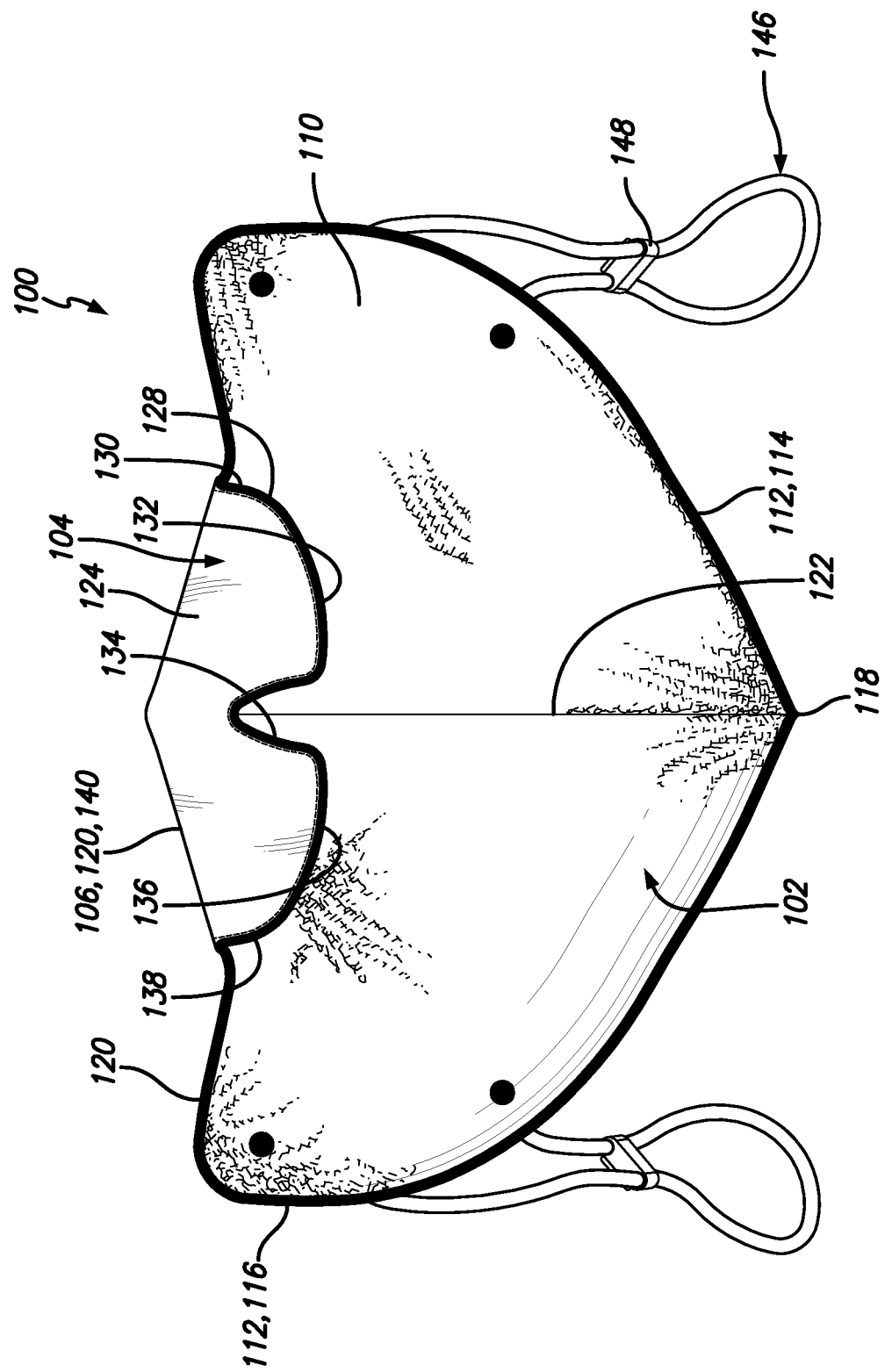
FIG. 5 is a back perspective view of the embodiment of the facial mask shown in FIG. 3.
Figure 6:
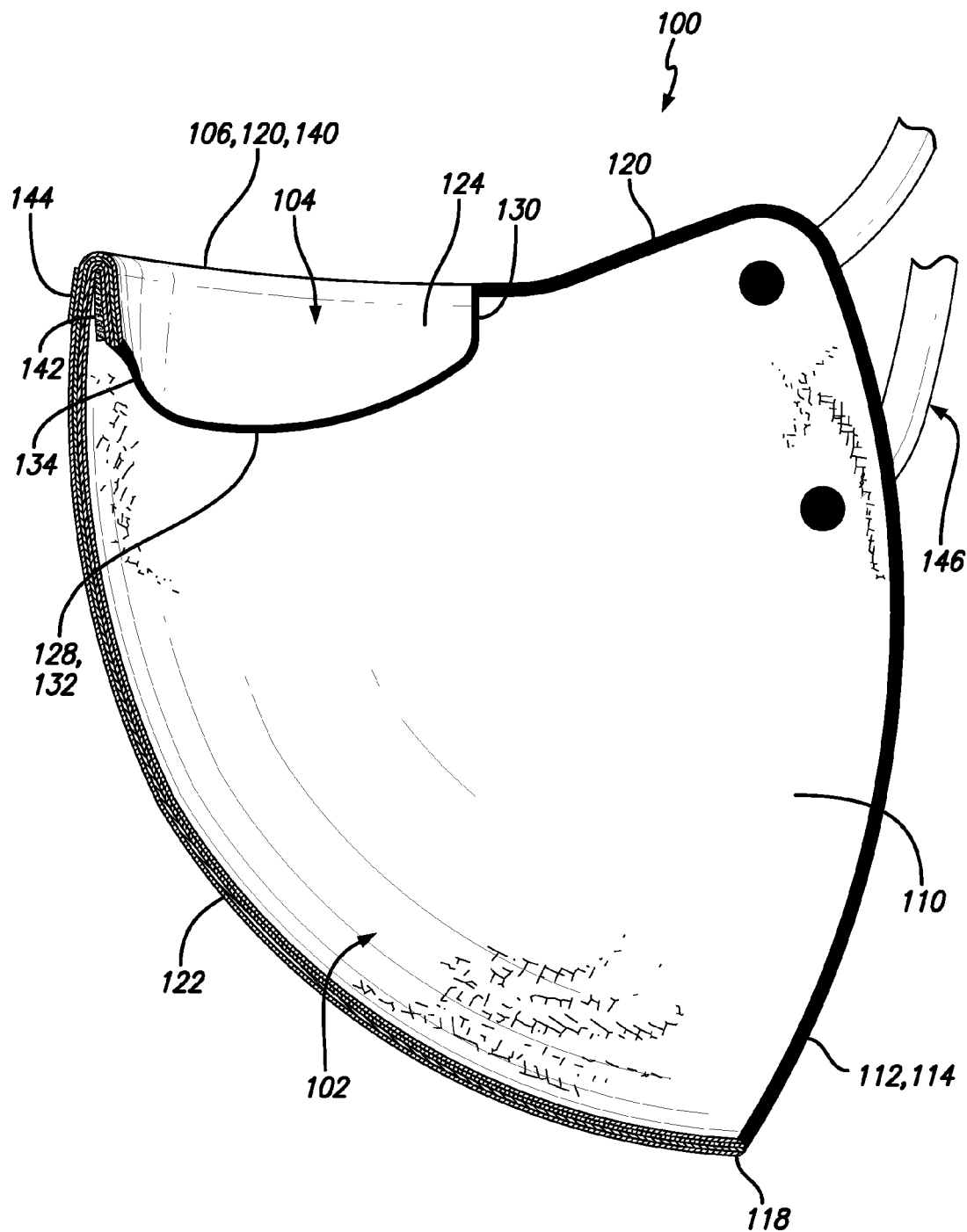
FIG. 6 is a partial, cutaway, lateral perspective view of the embodiment of the facial mask shown in FIG. 3 taken along the line 6-6.
Figure 7:
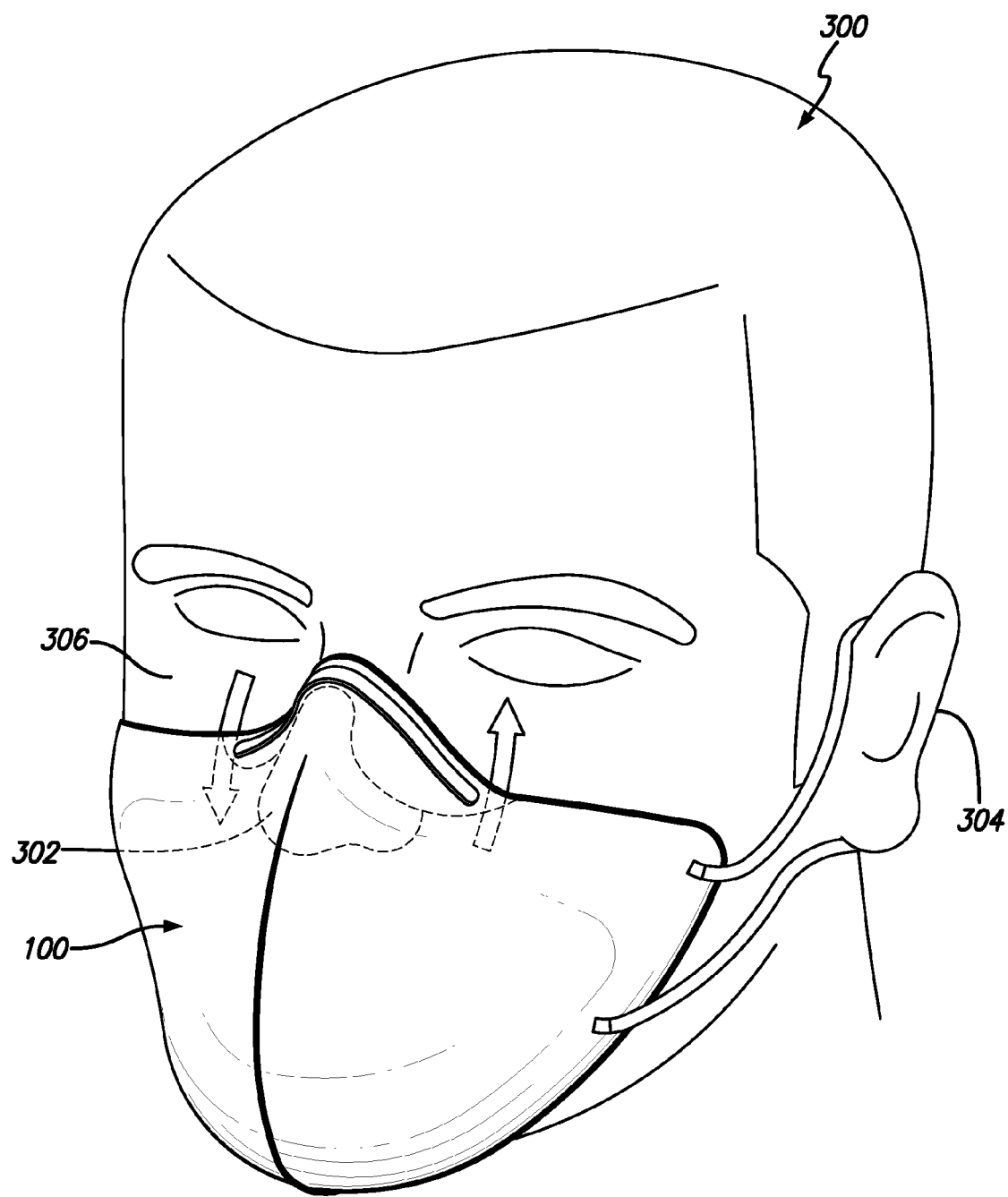
FIG. 7 is a frontal perspective view of the embodiment of the facial mask shown in FIG. 3 through FIG. 6 being worn by a wearer.

According to the present invention, there is provided a facial mask for decreasing the transmission of one or more than one human pathogen to and from a human wearer of the facial mask. Referring now to FIG. 3, FIG. 4, FIG. 5, FIG. 6, FIG. 7, and FIG. 8, there are shown, respectively, a frontal perspective view of one embodiment of a facial mask according to the present invention (FIG. 3); a frontal-lateral perspective view of the embodiment of the facial mask shown in FIG. 3 (FIG. 4); a back perspective view of the embodiment of the facial mask shown in FIG. 3 (FIG. 5); a partial, cutaway, lateral perspective view of the embodiment of the facial mask shown in FIG. 3 taken along the line 6-6 (FIG. 6); a frontal perspective view of the embodiment of the facial mask shown in FIG. 3 through FIG. 6 being worn by a wearer (FIG. 7); a back perspective view of part of the facial mask shown in FIG. 3 before final assembly (FIG. 8); and a partial, cutaway, frontal perspective view of the facial mask shown in FIG. 3 showing the multiple layers of the body of the facial mask (FIG. 9). As can be seen, the facial mask 100 comprises a body 102 for covering the mouth and nose 302 of a human wearer 300, and further comprises a flap 104 attached to the body 102 at a body-flap junction 106. The body 102 comprises a front surface 108 of the body 102, an opposing back surface 110 of the body 102, and a perimeter 112 of the body 102 defining a shape of the body 102. The shape of the body 102 can be any suitable shape for the purpose intended, as will be understood by those with skill in the art with reference to this disclosure. In one embodiment, the shape of the body 102 is selected from the group consisting of irregular, oval, rectangular, round, square and triangular. In a preferred embodiment, as shown most clearly in FIG. 3, the shape of the body 102 defined by the perimeter 112 of the body 102 comprises a right lateral edge 114 (orientation given from the wearer's perspective when wearing the mask), a left lateral edge 116 connected to the right lateral edge 114 at a bottom junction 118 of the perimeter 112, and a top edge 120 connecting the right lateral edge 114 to the left lateral edge 116, where the perimeter 112 of the body 102 when viewed from the front is essentially triangular in shape as shown. The top edge 120 partially forms the body-flap junction 106, as can be seen most clearly in FIG. 5 and FIG. 6. In one embodiment, the body 102 further comprises a central seam 122.

Referring again to FIG. 3, FIG. 5, FIG. 6 and FIG. 7, the flap 104 of the facial mask 100 comprises a front surface 124 (orientation given before folding the flap 104 into the final configuration of the facial mask 100) of the flap 104, an opposing back surface 126 of the flap 104, and a perimeter 128 of the flap 104 defining a shape of the flap 104. The shape of the flap 104 can be any suitable shape for the purpose intended, as will be understood by those with skill in the art with reference to this disclosure. In one embodiment, the shape of the flap 104 is selected from the group consisting of pentagonal, rectangular and triangular. In a preferred embodiment, as shown most clearly in FIG. 3, FIG. 5 and FIG. 7, the shape of the flap 104 defined by the perimeter 128 of the flap 104 is an inverted U-shape when looking at the front surface 108 of the body 102 or the back surface 108 of the body 102 with the bottom junction 118 oriented down. As used in this disclosure, the term "U-shape" is the shape of the flap 104 depicted in FIG. 3, FIG. 5 and FIG. 8 (but not inverted in FIG. 8). As can be seen particularly in FIG. 7, this inverted U-shape is particularly advantageous because it permits the flap to more closely approximate the nose 302 of a wearer 300 when the facial mask 100 is worn by the wearer 300 by compensating for the protrusion of the wearer's nose 302 at the base of the wearer's nose 302 than pentagonal, rectangular or triangular shapes. As can be seen most clearly in FIG. 5 and FIG. 8, in one embodiment of the present invention, the perimeter 128 of the flap 104 comprises in continuity from right to left (orientation given from the wearer's perspective when wearing the mask), a right vertical side 130, a right arcuate side 132, a central curved region 134, a left arcuate side 136, a left vertical side 138, and a base 140 partially forming the body-flap junction 106 and connecting the right vertical side 130 to the left vertical side 138.

Referring again to FIG. 3 and FIG. 6, in a preferred embodiment, the facial mask 100 further comprises a resilient member 142 attached to the body 102 or the flap 104. Incorporation of the resilient member 142 into the facial mask 100 is particularly advantageous because the resilient member 142 permits the facial mask 100 to more closely approximate the nose 302 of a wearer 300 when the facial mask 100 is worn by the wearer 300 by compensating for the various curves of the wearer's nose 302. In one embodiment, the resilient member 142 is attached to the back surface 20 of the body 12, or to the front surface 124 of the flap 104. In a preferred embodiment, however, as shown particularly in FIG. 6, the resilient member 142 is attached to the back surface 126 of the flap 104 because this orientation creates a better fit of the facial mask 100 for a greater number of potential wearers while exposing infectious particles that ingress or egress the facial mask 100 past the top edge 24 of the perimeter 22 of the body 12 to the front surface 124 of the flap 104 when the front surface 124 of the flap 104 comprises a fabric for use in decreasing the transmission of human pathogens that binds infectious particles as disclosed below. The resilient member 142 can comprise any substance suitable for the intended purpose, as will be understood by those with skill in the art with reference to this disclosure. In a preferred embodiment, the resilient member 142 is a sponge. In a preferred embodiment, the resilient member 142 comprises polyurethane.

Referring again to FIG. 3, FIG. 4, FIG. 6 and FIG. 7, in a preferred embodiment, the facial mask 100 further comprises a deformable strip 144 attached to the body 102 or the flap 104. The deformable strip 144 is particularly advantageous because the deformable strip 144 permits the facial mask 100 to be adjusted by a wearer 300 to more closely approximate the nose 302 of the wearer 300 when the facial mask 100 is worn by the wearer by compensating for the various curves of the wearer's nose 302. In one embodiment, the deformable strip 144 is attached to the back surface 20 of the body 12, or to the front surface 124 of the flap 104 or to the back surface 126 of the flap 104. In a preferred embodiment, as shown particularly in FIG. 4 and FIG. 6, the deformable strip 144 is attached to the front surface 108 of the body 102 near the top edge 24 overlying the flap, so that deforming the deformable strip 144 imparts deformation to the resilient member 142 and the remainder of the flap 104 also, as will be understood by those with skill in the art with reference to this disclosure. The deformable strip 144 comprises a substance which can be easily deformed by the wearer 300. The deformable strip 144 can comprise any substance suitable for the intended purpose, as will be understood by those with skill in the art with reference to this disclosure. In a preferred embodiment, the deformable strip 144 comprises plastic or comprises spring steel wires encased in plastic. In a preferred embodiment, the deformable strip 144 comprises a malleable aluminum.

Referring again to FIG. 3, FIG. 4, FIG. 5, FIG. 7 and FIG. 9 in a preferred embodiment, the facial mask 100 further comprises one or more than one extension 146 attached to the body 102 for securing the facial mask 100 to the head of a wearer 300. The extension 146 can comprise an elastic substance such as natural rubber, or synthetic rubber or other stretchable polymers, or can comprise a non-elastic substance such as non-elastic cloth or plastic, and can be in the form of ties that encircle the wearer's ears 304 or face 306 or ear loops, with or without adjusters 148 as shown in the Figures. In one embodiment, the one or more than one extension 146 is a series of adhesive strips to allow attachment of the facial mask 100 to a wearer's face 306.

Figure 10:
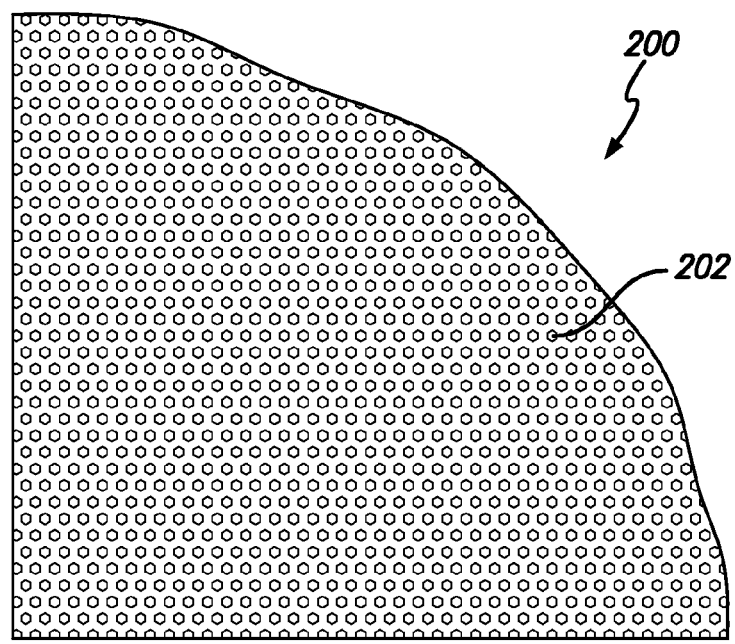
FIG. 10 is a partial, frontal perspective view of a fabric according to the present invention.

According to one embodiment of the present invention, there is provided a fabric for decreasing the transmission of one or more than one human pathogen. Referring now to FIG. 10, there is shown a partial frontal perspective view of the fabric according to the present invention. As can be seen, in one embodiment, the fabric 200 according to the present invention comprises binding substances 202. In another embodiment, the fabric 200 according to the present invention comprises a composition 202 for coating a polypropylene-based fabric or polypropylene-based material as disclosed in this disclosure. In one embodiment, the fabric comprises spunbond polypropylene fiber. In one embodiment, the density of the spunbond polypropylene fiber is between 10 g/m$^2$ and 50 g/m$^2$. In a particularly preferred embodiment, the density of the spunbond polypropylene fiber is 25 g/m$^2$. In another particularly preferred embodiment, the density of the spunbond polypropylene fiber is 45 g/m$^2$. According to another embodiment of the present invention, there is provided a device for decreasing the transmission of one or more than one human pathogen, where the device comprises a fabric 200 according to the present invention. In one embodiment, the device is a facial mask according to the present invention, such as a facial mask 100. In a particularly preferred embodiment, both the body 102 and the flap 104 comprise a fabric 200 according to the present invention.

Figure 11:
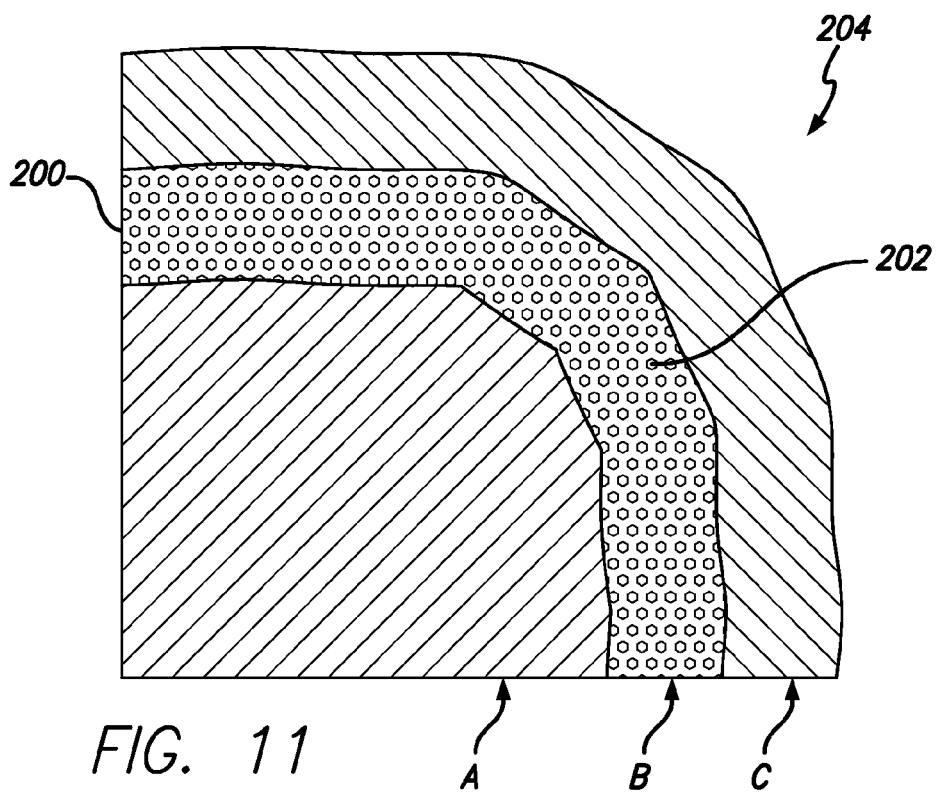
FIG. 11 is a partial, cutaway, frontal perspective view of a material according to the present invention, comprising the fabric shown in FIG. 10, and comprising three layers.
Figure 12:
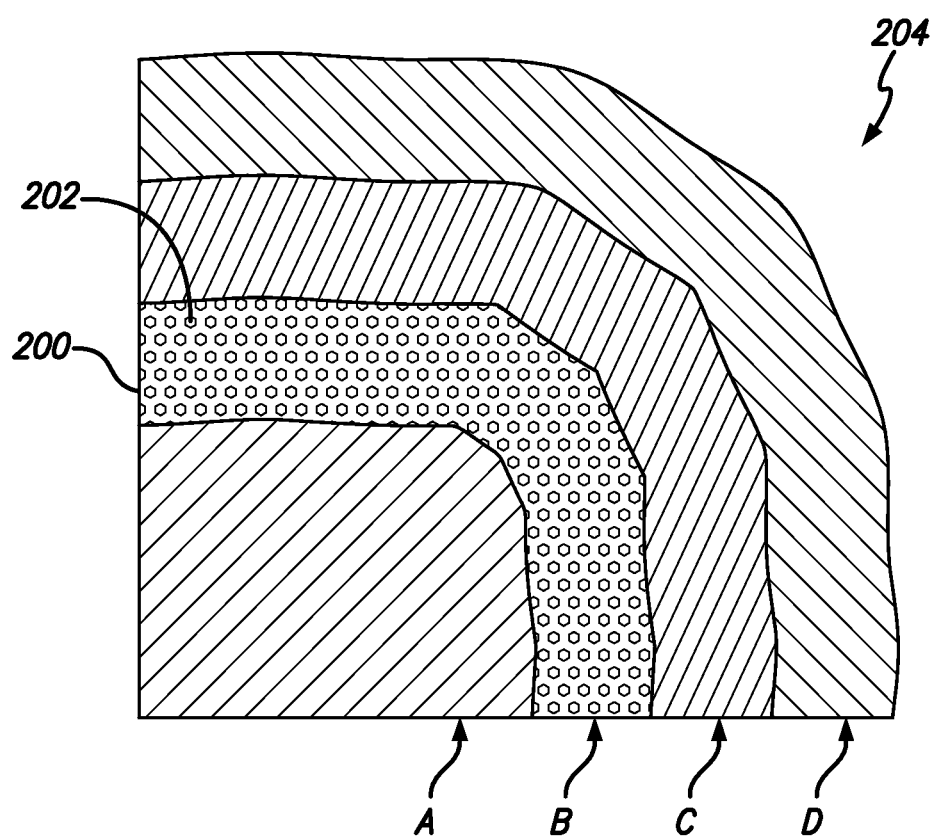
FIG. 12 is a partial, cutaway, frontal perspective view of another material according to the present invention, comprising the fabric shown in FIG. 10, and comprising four layers.

According to one embodiment of the present invention, there is provided a material for decreasing the transmission of one or more than one human pathogen. Referring now to FIG. 11 and FIG. 12, there is shown, respectively, a partial, cutaway, frontal perspective view of a material according to the present invention, comprising the fabric shown in FIG. 10, and comprising three layers (FIG. 11); and a partial, cutaway, frontal perspective view of another material according to the present invention, comprising the fabric shown in FIG. 10, and comprising four layers (FIG. 12). As can be seen, in one embodiment, the material 204 comprises a fabric 200 according to the present invention. According to another embodiment of the present invention, there is provided a device for decreasing the transmission of one or more than one human pathogen, where the device comprises a material 204 according to the present invention. In one embodiment, the device is a facial mask according to the present invention, such as a facial mask 100. In a particularly preferred embodiment, both the body 102 and the flap 104 comprise a material 204 according to the present invention.

The material 204 according to the present invention, comprises a plurality of layers, where one or more than one layer comprises the fabric 200. The material 204 can comprise two layers, three layers, four layers or more than four layers, as will be understood by those with skill in the art with reference to this disclosure. In a particularly preferred embodiment, the plurality of layers is three layers (as shown in FIG. 11, designated here A, B and C). In another particularly preferred embodiment, the plurality of layers is four layers (as shown in FIG. 12, designated here A, B, C and D). In a particularly preferred embodiment, the body 102 and flap 104 of the facial mask 100 comprises a material 204 according to the present invention and both the front surface 108 of the body 102 and the front surface 124 of the flap 104 comprise a fabric 200 according to the present invention.

At least one of the layers of the material 204 comprises a fabric 200 (shown in FIG. 11 and FIG. 12 as layer B) according to the present invention. In a preferred embodiment, two of the layers of the material 204 comprise a fabric 200. In one embodiment, one or more than one of the layers of the material 204 is a heat-moldable fabric, such as a heat-moldable fabric selected from the group consisting of polypropylene, polyester and non-woven cellulose acetate fabric. In one embodiment, the heat-moldable fabric is selected from the group consisting of spunbond nonwoven polypropylene fiber (SBPF) (also called spunbonded non-woven polypropylene), and melt blown polypropylene fiber (MBPF). In one embodiment, the heat-moldable fabric comprises a spunbond/melt blown fiber composite comprising alternating spunbond (S) and melt blown layers (M), such as for example MS, SM, SMS, SSMS, SMSS, SMSMS, SMMSS and SSMMS. Such heat-moldable layers permit shaping of facial masks with heat or ultrasonic welding according to the present invention. In addition, such heat-moldable layers trap airborne particles, but is hydrophobic so that infectious particle-laden droplets are normally not disrupted even if the infectious particle-laden droplets are trapped within the layer allowing the fabric 200 according to the present invention to bind the infectious particles. Further, the hydrophobic layer repels moisture, and hence when the back surface 110 of the body 102 is a hydrophobic layer, the wearer 300 of the facial mask 100 will not feel moisture or wetness against their face 306.

In a preferred embodiment, as shown in FIG. 11, the material 204 comprises three layers, a first layer of spunbond polypropylene fiber (layer A), a second layer of fabric according to the present invention (layer B), and a third layer of melt-blown polypropylene fiber (layer C). In one embodiment, the density of the spunbond polypropylene fiber is between 10 g/m$^2$ and 50 g/m$^2$. In a particularly preferred embodiment, the density of the spunbond polypropylene fiber is 25 g/m$^2$. In another particularly preferred embodiment, the density of the spunbond polypropylene fiber is 45 g/m$^2$. In one embodiment, the density of the melt-blown polypropylene fiber is between 15 g/m$^2$ and 25 g/m$^2$. In a particularly preferred embodiment, the density of the melt-blown polypropylene fiber is 18 g/m$^2$. In a particularly preferred embodiment, as shown in FIG. 11, the material 204 comprises three layers, a first layer of spunbond polypropylene fiber (layer A) having a density of 45 g/m$^2$, a second layer of fabric according to the present invention (layer B), a third layer of spunbond/melt blown fiber composite (layer C) having a density of 18 g/m$^2$.

In a preferred embodiment, as shown in FIG. 12, the material 204 comprises four layers, a first layer of spunbond polypropylene fiber (layer A), a second layer of fabric according to the present invention (layer B), a third layer of melt-blown polypropylene fiber (layer C), and a fourth layer of spunbond polypropylene fiber (layer D). In one embodiment, the density of the spunbond polypropylene fiber is between 10 g/m$^2$ and 50 g/m$^2$. In a particularly preferred embodiment, the density of the spunbond polypropylene fiber is 25 g/m$^2$. In another particularly preferred embodiment, the density of the spunbond polypropylene fiber is 45 g/m$^2$. In one embodiment, the density of the melt-blown polypropylene fiber is between 15 g/m$^2$ and 25 g/m$^2$. In a particularly preferred embodiment, the density of the melt-blown polypropylene fiber is 18 g/m$^2$. In a particularly preferred embodiment, as shown in FIG. 12, the material 204 comprises four layers, a first layer of spunbond polypropylene fiber (layer A) having a density of 45 g/m$^2$, a second layer of fabric according to the present invention (layer B), a third layer of melt-blown polypropylene fiber (layer C) having a density of 18 g/m², and a fourth layer of spunbond polypropylene fiber (layer D) having a density of 25 g/m².

In one embodiment, the fabric 200 according to the present invention comprises one or more than one binding substance 202 that binds one or more than one type of human pathogen. In a preferred embodiment, the fabric 200 comprises one or more than one binding substance 202 that binds one or more than one type of virus, such as influenza virus, that causes human respiratory tract infections such as influenza. By binding the human pathogen to the fabric 200 of the facial mask 100 of the present invention, the fabric 200 decreases the transmission of the human pathogen, such as for example by preventing release of virus particles when virus-laden droplets evaporate within the fabric 200.

The one or more than one binding substance 202 comprises one or more than one human pathogen binding group for chemically attaching the human pathogen to the binding substance, as will be understood by those with skill in the art with reference to this disclosure. In a preferred embodiment, the binding substance 202 further comprises a linker group (such as for example a vinyl sulfone group) for attaching the binding substance 202 to the fabric 200.

By way of example, in one embodiment, the human pathogen to be bound to the fabric 200 is selected from the group consisting of adeno-associated virus (AAV), herpes simplex virus (HSV), human papillomavirus (HPV), influenza viruses, rabies virus, respiratory syncytial virus (RSV), and the human pathogen binding group is a sialic acid group because these virus particles bind to human cells through a terminal sialic acid group on a surface oligosaccharide of the cell membrane of human cells. Sialic acid groups are, however, relatively expensive to produce in a form suitable for attachment to fibers or fabrics, and therefore, in a preferred embodiment, the binding substance 202 is a substance that mimics the binding action of sialic acid groups on influenza viruses, but that is cost effective as a component for industrial-scale production of fabrics comprising the binding substance according to the present invention.

According to one embodiment of the present invention, the one or more than one binding substance 202 comprises a human pathogen binding group selected from the group consisting of a sulfate group (such as for example, sulfated monosaccharide or sulfated oligosaccharide) and a sulfonate group (such as for example sulfonated monosaccharide or sulfonated oligosaccharide), because both sulfate groups and sulfonate groups mimic the binding action of sialic acid groups on adeno-associated virus (AAV), herpes simplex virus (HSV), human papillomavirus (HPV), influenza viruses, rabies virus, respiratory syncytial virus (RSV), as well as other human pathogens, while sulfate groups and sulfonate groups can be directly linked to free hydroxyl groups and free amino groups on fibers or fabrics in a cost-effective manner for industrial-scale production in fabrics 200 according to the present invention. In a preferred embodiment, the fabric 200 is a cellulosic fabric (i.e., comprises cellulose) and the one or more than one binding substance 202 comprises a human pathogen binding group comprising a sulfate group, yielding a fabric comprising a non-hydrogel cellulose sulfate.

According to another embodiment of the present invention, the human pathogen binding group is one or more than one reactive dye comprising one or more than one sulfonate group. In a preferred embodiment, the fabric 200 is a cellulosic fabric (i.e., comprises cellulose) and the binding substance 202 is one or more than one reactive dye comprising a sulfonate group, yielding a fabric 200 comprising a cellulose sulfonate.

Reactive dyes are a class of substances used to dye fibers and fabrics, both cellulosic fibers and cellulosic fabrics (such as acetate, cotton and rayon), and non-cellulosic fibers and non-cellulosic fabrics (such as wool and nylon, and fabrics made from polyester or polyolefin). Reactive dyes comprise a reactive linker group, usually either a haloheterocycle or an activated double bond that, when applied to a fiber in a dye bath, forms a covalent chemical bond with an hydroxyl group on the fiber or the fabric. Reactive dyes are classified according to the category of linker group that attaches the dye to the fiber or fabric. In one embodiment, the binding substance is one or more than one reactive dye selected from the group consisting of aminochlorotriazine (Procion7 H), aminochlorotriazine-sulfatoethylsulfone (Sumafix Supra), aminofluorotriazine (Cibachron F), aminofluorotriazine-sulfatoethylsulfone (Cibacron C), bis(aminochlorotriazine) (Procion7 H-E) bis(aminonicotinotriazine) (Kayacelon React7), chlorodifluoropyrimidine (Drimarine K), dichloroquinoxaline (Levafix7 E), dichlorotriazine (Procion MX), sulfatoethylsulfone (vinyl sulfone; Remazol7), sulfatoethylsulfonamide (Remazol7 D), trichloropyrimidine (Drimarine X). Reactive Dyes further comprise a chromophore group, providing the specific color for the dye. The chromophore group commonly comprises a multi-ring aromatic group; however, multi-ring aromatic groups tend to decrease water solubility, so reactive dyes usually further comprise one or more sulfonate groups to increase water solubility. The sulfonate groups of reactive dyes can function as the human pathogen binding group of the binding substance of the fabrics of the present invention, while the reactive linker groups of the reactive dyes can function as the linker group of the binding substance.

A given dye frequently has several trade names, but the generic names (Color Index; CI) for dyes comprise the following format: [Category (acidic, basic, direct or reactive); Color; and Number]. According to one embodiment of the present invention, the one or more than one binding substance 202 is a reactive dye selected from the group consisting of CI Reactive Blue 4, CI Reactive Blue 21, CI Reactive Blue 140, CI Reactive Blue 163, CI Reactive Brown 23, CI Reactive Orange 4, CI Reactive Red 1, CI Reactive Red 2, CI Reactive Red 6, CI Reactive Red 11, CI Reactive Red 78, CI Reactive Yellow 39, and CI Reactive Yellow 86, each of which comprises sulfonate groups which function as the human pathogen binding group suitable for binding one or more than one human pathogen according to the present invention, and each of which further comprises a linker group suitable for attaching the binding substance (the dye) to the fabric. In a particularly preferred embodiment, the binding substance is Reactive Blue 21 [copper, (29H,31H-phthalocyaninato(2)-$N^{29}$,$N^{30}$,$N^{31}$,$N^{32}$)-, sulfo ((4-((2-sulfooxy)ethyl)sulfonyl)phenyl)amino) sulfonyl derivs] (CAS Reg. No. 73049-92-0), a sulfonated copper phthalocyanine dye with a vinyl sulfone linker group that attaches the dye to fibers and fabrics, including cellulosic fibers and fabrics. The appropriate reaction conditions for attaching reactive dyes, including for attaching CI Reactive Blue 21, to fibers and fabrics are well known to those with skill in the art, and can be found in instructions from the dye manufacturers, as well as in standard textile references, as will be understood by those with skill in the art with reference to this disclosure.

As will be understood by those with skill in the art with reference to this disclosure, the binding substance 202 cannot render the fabric impermeable to gases when the fabric 200 is to be incorporated into the body of a facial mask 100 according to the present invention because such impermeability would render the facial mask 100 non-functional, as will be understood by those with skill in the art with reference to this disclosure. For example, if the human pathogen binding group is a sulfate group, the sulfate group cannot form a cellulose sulfate hydrogel within the fabric because cellulose sulfate hydrogels would block the passage of air through a facial mask rendering the facial mask non-functional and, therefore, the use of the term "cellulose sulfate" and its related terms when referencing the content of a fabric according to the present invention is understood not to comprise a cellulose sulfate hydrogel or any form that is impermeable to gas that would block the passage of air through a facial mask rendering the facial mask non-functional (that is, rendering a wearer unable to breathe adequately through the facial mask). Using a reactive dye as the binding substance 202 in the fabric 200 of the facial mask 100 according to the present invention is particularly advantageous because the amount of reactive dye binding to a fabric is never high enough to cause the sulfonate groups in the reactive dyes to make a hydrogel in the fabric.

As will be understood by those with skill in the art with reference to this disclosure, both cellulose sulfate and cellulose sulfonate have surfactant properties, so that fabrics 200 comprising cellulose sulfate or cellulose sulfonate disrupt virus-laden droplets and exposes the virus particles to the sulfate groups on the cellulose sulfate, and to the sulfonate groups on the cellulose sulfonate, thereby trapping the virus particles within the fabric 200.

In one embodiment, the fabric 200 further comprises one or more than one additional substance, other than the binding substance 202 and the fibers of the fabric 200, that decreases the pathogenic capacity of one or more than one human pathogen. In a preferred embodiment, the one or more than one additional substance is one or more than one type of multivalent metallic ion, such as for example multivalent copper, multivalent silver or multivalent zinc, all of which are antibacterial, antifungal and antiviral. In a particularly preferred embodiment, the metallic salt is a divalent metallic salt, such as one or more than one divalent metallic salt selected from the group consisting of a salt of divalent copper and a salt of divalent zinc. In another embodiment, the one or more than one substance is a metallic salt, such as for example a metallic salt selected from the group consisting of copper acetate, copper oxide, copper sulfate and zinc acetate all of which are bactericidal, viricidal and fungicidal.

As will be understood by those with skill in the art with reference to this disclosure, using a binding substance 202 comprising a sulfate group or a sulfonate group on a fabric 200 comprising cellulose is both relatively inexpensive and suitable for industrial-scale production of facial masks 100 according to the present invention to protect large populations from the transmission of influenza viruses and other human pathogens. Further, the fabric 200 is safe to both people and pets, for example by replacing toxic antimicrobial compounds used in some facial masks, and by binding the virus particles within the fabric 200 so that the virus particles do not leach out of the fabric 200 after the virus particles contact the fabric 200. Further advantageously, the fabric 200 does not require illumination and singlet oxygen generation for decreasing the transmission of one or more than one human pathogen, as with some fabrics designed to decrease transmission of one or more than one human pathogen.

In one embodiment, the fabric 200 is woven, such as for example woven rayon. In another embodiment, the fabric 200 is non-woven, such as for example non-woven rayon. According to one embodiment of the present invention, the facial mask 100 comprises a fabric 200 for use in decreasing the transmission of one or more than one human pathogen according to the present invention. In one embodiment, facial mask 100 comprises a fabric 200 as disclosed in this disclosure and as shown in FIG. 10. In another embodiment, facial mask 100 comprises a material as disclosed in this disclosure and as shown in FIG. 11 and FIG. 12.

According to another embodiment of the present invention, there is provided a method for making a fabric 200 for use in constructing a facial mask 100 according to the present invention for decreasing the transmission of one or more than one human pathogen, such as for example viruses that cause human respiratory tract infections. In one embodiment, the method produces a fabric 200 according to the present invention. The method will now be disclosed by way of example only primarily with respect to making a fabric comprising cellulose (in this example, rayon) with binding substances comprising sulfate groups as the human pathogen binding group, though other methods can be used to produce the same fabric, and corresponding fabrics with other binding substances (such as sulfonate groups) according to the present invention, as will be understood by those with skill in the art with reference to this disclosure.

In one embodiment, the method comprises, first, providing fibers suitable for use in a fabric 200 for decreasing the transmission of one or more than one human pathogen. In one embodiment, the fabric comprises cellulose. In a preferred embodiment, the fabric comprises rayon (a form of cellulose). The most important source of cellulose fibers for commercial purposes is from wood pulp; however, cellulose fibers obtained directly from wood pulp are too short and coarse to weave into a fabric according to the present invention, and cellulose derived from wood pulp is relatively insoluble in organic solvents and cannot be extruded into fine fibers. By contrast, rayon fibers are produced from naturally occurring cellulose polymers derived from wood pulp and other plants. To form rayon fibers, the cellulose is first derivatized with solubilizing groups (such as for example acetate), formed into spun fibers, and then, the solubilizing groups are removed yielding cellulose fibers that can be woven into fabric, as will be understood by those with skill in the art with reference to this disclosure.

Next, the method comprises adding one or more than one binding substance to the fibers. Adding the binding substance to the fibers can be accomplished using techniques known to those with skill in the art, as will be understood by those with skill in the art with reference to this disclosure. In a preferred embodiment, the binding substance added is a binding substance according to the present invention. By way of example, the method will be disclosed with respect to binding substances comprising a human pathogen binding group that comprises a sulfate group, thereby yielding sulfated cellulose fibers. In this embodiment, adding one or more than one binding substance to the fibers results in sulfation of the cellulose derived fibers in the fabric without disrupting the structure or strength of the fabric. Further, though these steps are disclosed with respect to covalently bonding sulfate groups to cellulosic fibers (such as rayon), equivalent steps can be used for adding sulfate groups to other cellulosic fabrics, blends of cellulose-derived and noncellulose-derived fibers (such as for example fibers made from polyester or polyolefin) and noncellulose-derived fibers that comprise free hydroxyl or amino groups, as will be understood by those with skill in the art with reference to this disclosure.

Cellulose is a linear polymer of glucose units, each of which has three free hydroxyl groups. The degree of sulfation (DS) of cellulose is defined in the art as the average number of sulfate groups per monosaccharide unit. A DS of 3 is the maximum possible, indicating that all available hydroxyl groups are fully sulfated. A degree of sulfation of 1 indicates that an average of one sulfate group per glucose unit is present, and a DS of 0.1, for example, indicates that an average of one hydroxyl group of every ten glucose units is sulfated. An important aspect of the present invention is that the binding of viruses and other human pathogens to a fiber or fabric according to the present invention involves binding of the human pathogen to more than one immobilized sulfate group or sulfonate group on the fiber or fabric, thereby strongly increasing the affinity of the interaction between the binding substance and the human pathogen.

The degree of sulfation is determined by any suitable analytical method that measures sulfate, sulfonate or total sulfur, such as for example by elemental analysis. The sulfur content of cellulose fibers without a binding substance attached or nonpigmented cellulose fibers or fabrics is extremely low or undetectable. According to one embodiment of the present invention, the present method results in a degree of sulfation between 0.02 and 2. In a preferred embodiment of the present invention, the present method results in a degree of sulfation between 0.05 and 0.5. In a particularly preferred embodiment, the present method results in a degree of sulfation of between 0.09 and 0.21. The degree of sulfation for sulfated or sulfonated fibers or fabric can be regulated by adjusting the time, temperature or reagent concentrations in a sulfation or sulfonation reaction, as will be understood by those with skill in the art with reference to this disclosure, to produce fibers with the required degree of sulfation.

As the degree of sulfation increases above 0.2 for a cellulosic fabric, the water solubility of fibers increases when exposed to liquid water or water vapor, causing the fabric to form a hydrogel and decrease gas permeability through the fabric. This tendency to solubilize is not acceptable for a fabric used in a facial mask where relatively unobstructed passage of air is required. Therefore, in one embodiment of the present invention, the method further comprises crosslinking the fibers of the fabric, before or after attaching the binding substance, by treating the fabric with one or more than one crosslinking agent that chemically bonds the fibers of the fabric to one another thereby preventing solubilization. In one embodiment, treating the fabric with a crosslinking agent comprises contacting the fabric with an alkali, e.g., sodium hydroxide, to give the alkalinized cellulose in the case of cellulosic fabrics, and then reacting the fabric with the crosslinking agent. In one embodiment, the crosslinking agent is selected from the group consisting of dichloroalkanes, dimethylolureas, formaldehyde and trimethylol-melamines. In a preferred embodiment, the crosslinking agent is an epoxy compound selected from the group consisting of diethylene glycol diglycidyl ether, ethylene glycol diglycidyl ether, epichlorohydrin, glycerin diglycidyl ether and vinylcyclohexene dioxide.

Adding one or more than one binding substance comprising a sulfate human pathogen binding group to the fibers can be accomplished, for example, by first, contacting the fabric with a suitable solvent, such as for example dimethylsulfoxide (DMSO) or dimethylformamide (DMF). The amount of time that the fabric is contacted with the solvent is adjusted to optimize fiber swelling, thereby increasing exposure of hydroxyl groups on the fiber surface to sulfation, as will be understood by those with skill in the art with reference to this disclosure.

Next, the solvent treated fabric is contacted with the binding substance, such as for example a sulfating reagent. Suitable sulfating reagents depend on the solvent used, as will be understood by those with skill in the art with reference to this disclosure. For example, in one embodiment, the solvent is dimethylsulfoxide, and the sulfating reagent is DMSO treated with sulfur trioxide (DMSO-$SO_3$). In another embodiment, the solvent is dimethylformamide, and the sulfating reagent is dimethylformamide treated with sulfur trioxide (DMF-$SO_3$). Contact with the binding substance is maintained until a satisfactory degree of covalent binding of the binding substance to the fibers is achieved but before excess binding substance binds to the fibers, which in the case of sulfate would render the fabric impermeable to gas upon contact with liquid water or water vapor, as will be understood by those with skill in the art with reference to this disclosure.

In one embodiment, the method further comprises rinsing the fabric with a solvent, such as for example (DMSO-$SO_3$) and (DMF-$SO_3$) and then contacting the fabric with a suitable base, such as for example sodium hydroxide, sodium acetate, or sodium bicarbonate, to neutralize an acidic binding substance such as an acidic sulfating agent, or to neutralize acid formed during the addition of the binding substance to the fabric.

The fabric is then washed with a suitable solvent, such as for example water or a simple alcohol (ethanol or isopropanol) to remove unreacted reagents yielding the sulfated fabric suitable for use in decreasing the transmission of one or more than one human pathogen, including viruses that cause human respiratory tract infections.

In another embodiment, the method for making a fabric for use in constructing a facial mask according to the present invention for decreasing the transmission of one or more than one human pathogen, comprises, first, providing cellulose sulfate material made from cellulose pulp or cellulose powder and having a degree of sulfation greater than 0.2, and preferably greater than 0.5 sufficient to render the fibers water soluble. Next, the soluble cellulose sulfate is then applied to a fabric and covalently linked to the fibers of the fabric with a crosslinking agent, as disclosed above, as will be understood by those with skill in the art with reference to this disclosure. In this embodiment of the method, the fabric is not exposed to the relatively harsh sulfation conditions and reagents, but only to soluble cellulose sulfate and to the crosslinking reagents, and to the conditions for crosslinking, thereby reducing the potential for damage to the fabric that can occur if the sulfation reaction is not well controlled. A concentration of soluble cellulose sulfate is selected by testing, such that a fabric with acceptable pressure drop characteristics suitable for gas exchange through a facial mask is obtained, especially when the fabric is to be used in a mask according to the present invention, as will be understood by those with skill in the art with reference to this disclosure.

In one embodiment of the present invention, the method further comprises contacting the fabric with one or more than one substance that chemically disrupts a characteristic of the human pathogen essential for human pathogenicity. In a preferred embodiment, the one or more than one substance is a multivalent metallic ion, such as for example multivalent copper, multivalent silver or multivalent zinc, all of which are antibacterial, antifungal and antiviral. In another embodiment, the one or more than one substance is a metallic salt, such as for example copper oxide, zinc acetate, copper acetate or copper sulfate, all of which are bactericidal, viricidal and fungicidal. In a preferred embodiment, the metallic salt is a divalent metallic salt. Acetate is advantageous as an anionic salt constituent as it is volatile and can be removed from the fabric by evaporation, but other anions are also suitable as salt components, including chlorides, oxides, iodides and others. The addition of the one or more than one substance to the fabric increases the effectiveness of the facial mask of the present invention in decreasing the transmission of one or more than one human pathogen by using mechanisms in addition to binding the human pathogen to the fabric.

In one embodiment of the present invention, the method further comprises incorporating one or more than one type of fiber other than the fibers comprising the binding substance, such as for example polyester fibers or polypropylene fibers, into the fabric.

In another embodiment, cellulosic fibers in the form of staple or tow are sulfated by the same types of sulfation reactions used for fabrics as disclosed in this disclosure, and then the cellulose sulfate fibers are washed and then formed into a nonwoven or woven fabric by conventional methods whereby cellulosic staple or tow are spun into threads or directly formed into nonwoven fabrics.

The method of the present invention for making a fabric 200 for use in constructing a facial mask 100 according to the present invention for decreasing the transmission of one or more than one human pathogen, will now be disclosed with respect to the following examples.

Example 1

Preparation of Sulfated Rayon Fabric

According to one embodiment of the present invention, sulfated rayon was prepared according to the present invention as follows. First, 60 ml isopropanol was chilled on ice and 0.2 grams $MgSO_4$ was added to the isopropanol to remove water. Next, 240 ml sulfuric acid, previously chilled on ice, was added to the isopropanol. Then, nonwoven rayon fabric having a density of 70 grams/meter$^2$ was cut into 17.5 cm by 22.5 cm rectangles and laid on polypropylene mesh of approximately the same size. Next, the rayon fabric on the mesh was submerged in chilled acetic acid for 15 minutes. Then, the isopropanol/sulfuric acid mixture was poured into a polyethylene box (approximately 30 cm by 37.5 cm) sitting on ice. Next, the rayon fabric on the polyethylene mesh was submerged in the isopropanol/sulfuric acid mixture for either 5 minutes or for 10 minutes, and rinsed first in cold isopropanol, and then in cold isopropanol containing 3 grams of sodium acetate per 100 ml, and then in cold isopropanol producing the sulfated rayon fabric. Next, the rayon fabric was then allowed to dry while still on the polyethylene mesh. Samples of the sulfated rayon fabric were analyzed for sulfur and carbon content. A 5 minute reaction time prior to rinsing was found to yield a degree of sulfation (DS) of approximately 0.1, while a 10 minute reaction time prior to rinsing was found to yield a degree of sulfation (DS) of approximately 0.2.

Example 2

Preparation of Sulfonated Rayon Fabric

According to one embodiment of the present invention, sulfonated rayon fabric was prepared according to the present invention as follows. First, a solution was prepared by adding 30 grams of sodium sulfate to 600 grams distilled water, followed by adding of 4 grams of CI Reactive Blue 21 dye (a sulfonated binding substance). Next, 30 grams of nonwoven rayon fabric having a density of 70 grams/meter$^2$ were added to the solution and gently swirled until uniformly submerged and wetted. Then, 12 grams of sodium carbonate were added with stirring, and the mixture was held at 30 EC for 35 minutes. Next, the temperature was raised to 70 EC for an additional 60 minutes yielding the sulfonated rayon fabric (with CI Reactive Blue 21 dye as the binding substance). Then, the sulfonated rayon fabric was rinsed under running water until no more free dye was eluted, and the sulfonated rayon fabric was air-dried.

Example 3

Preparation of Fabric Comprising One or More than One Substance that Destroys the Pathogenic Capacity of One or More than One Human Pathogen According to one embodiment of the present invention, sulfated cellulose fabric made according to Example 1 or sulfonated cellulose fabric made according to Example 2 was prepared to comprise one or more than one than one additional substance, other than the binding substance, that destroys the pathogenic capacity of one or more than one human pathogen as follows. First, sulfated rayon fabric was made according to the process disclosed in Example 1, or sulfonated rayon fabric (with CI Reactive Blue 21 dye as the binding substance) was made according to the process disclosed in Example 2. Then, copper sulfate and zinc acetate, both of which are divalent metal salts, were applied by aerosol to the fabric at 40 µl/cm$^2$ fabric using a concentration of 1 gram metal salt/100 milliliters of water. The fabric comprising the additional substance was then air-dried yielding sulfated rayon fabric comprising both divalent copper and divalent zinc ions, or sulfonated rayon fabric comprising both divalent copper and divalent zinc ions.

Example 4

Industrial Process for Preparation of Sulfonated Rayon Fabric Comprising Divalent Metal Salts According to one embodiment of the present invention, sulfonated rayon fabric (with CI Reactive Blue 21 dye as the binding substance) and comprising divalent metal salts was prepared according to the present invention as follows. First, 100% spunlace viscose rayon fabric having a density of 70 grams/meter$^2$ was dyed with CI Reactive Blue 21 (Novacron7 Turquoise H-GN) at a liquid to solid ratio of 20:1. Next, 50 g/L sodium sulfate, 20 g/L sodium carbonate and 12% dye by volume (120 ml/L) was added to a dye bath and mixed thoroughly with continuous agitation. Then, the rayon fabric was immersed in the dye bath for 35 minutes at a temperature of 30 EC, followed by 60 minutes at a temperature of 70 EC producing the sulfonated rayon fabric (with CI Reactive Blue 21 dye as the binding substance). Next, the sulfonated rayon fabric was rinsed under running water and air-dried. Then, 50 grams each of copper acetate and zinc acetate per liter of water was sprayed on the sulfonated rayon at rate 0.08 L/m$^2$ producing the sulfonated rayon fabric comprising both divalent copper and divalent zinc ions. The sulfonated rayon fabric comprising both divalent copper and divalent zinc ions was again air-dried.

Example 5

Assessment of Fabric for Anti-Human Pathogen Properties

Testing antiviral properties (as a surrogate for anti-human pathogen properties) of a fabric is performed by application of standardized amounts of a virus onto a piece of test fabric. The test fabric is then stirred in cell culture medium to elute any functional virus particles, that is, virus particles that are not inactivated by adherence to the fabric or otherwise to the test fabric. Functional virus particles eluted into the culture medium are assayed for viral activity by contacting the medium with cells susceptible to viral killing, and ascertaining a quantitative readout of cell death. Decreased cell death in the eluting medium indicates increased inactivation of the virus by the test fabric through viral adherence to the fabric or otherwise by the test fabric.

According to one embodiment of the present invention, sulfated rayon fabric having a degree of sulfation (DS) of 0.2, made according to Example 1, sulfonated rayon fabric (with CI Reactive Blue 21 dye as the binding substance), made according to Example 2, and sulfonated rayon fabric (with CI Reactive Blue 21 dye as the binding substance) comprising both copper sulfate and zinc acetate, made according to Example 3, were assessed for antiviral properties. First, test samples of the sulfated rayon fabric, the sulfonated rayon fabric (with CI Reactive Blue 21 dye as the binding substance), and the sulfonated rayon fabric (with CI Reactive Blue 21 dye as the binding substance) comprising both copper sulfate and zinc acetate were submitted to Microbiotest, Inc. (Sterling, Va. US) for assessment of the fabric's ability to inactivate the human pathogen herpes simplex virus (HSV). HSV was applied in an aerosol to a 5 cm by 5 cm area of the test fabrics, as well as to a non-sulfated, non-sulfonated piece of rayon control fabric, and to a piece of rayon fabric treated only with copper sulfate and zinc acetate (1 gram each per 100 ml water, applied at 40 microliters per square centimeter). The HSV-treated fabric samples were held for 1 minute and then placed in individual 20 ml aliquots of extraction medium and subjected to gentle agitation for 5 minutes. Aliquots of the extraction sample were serially diluted 10-fold in dilution medium and inoculated onto host cells. Residual infectious virus in extraction medium from each sample was detected and quantified by their viral-induced cytopathic effects.

TABLE 1

RESULTS OF ASSESSMENT OF FABRIC FOR ANTIVIRAL PROPERTIES

| FABRIC TESTED | LOGS OF INFECTIOUS HSV RECOVERED AFTER 1 MINUTE VIRUS CONTACT TIME WITH THE FABRIC |
|---|---|
| non-sulfated, non-sulfonated rayon control fabric | 7.60 ± "0.19 |
| non-sulfated, non-sulfonated rayon fabric treated with copper sulfate and zinc acetate | 5.60 ± 0.23 |
| sulfated rayon fabric | 5.73 ± 0.24 |
| sulfonated rayon fabric (with CI Reactive Blue 21 dye as the binding substance) | 7.23 |

TABLE 1-continued

RESULTS OF ASSESSMENT OF FABRIC FOR ANTIVIRAL PROPERTIES

| FABRIC TESTED | LOGS OF INFECTIOUS HSV RECOVERED AFTER 1 MINUTE VIRUS CONTACT TIME WITH THE FABRIC |
|---|---|
| sulfonated rayon fabric (with CI Reactive Blue 21 dye as the binding substance) comprising copper sulfate and zinc acetate | undetectable (below 3.13) |

As can be seen, the sulfated rayon fabric prepared according to Example 1, had a 1.87 log reduction in pathogenic virus as compared to the non-sulfated, non-sulfonated rayon control fabric. Incorporating copper sulfate and zinc acetate to the non-sulfated, non-sulfonated rayon control fabric yielded a 2.0 log reduction in pathogenic virus as compared to the non-sulfated, non-sulfonated rayon control fabric, where the reduction in pathogenic virus was attributable to the presence of the divalent salts alone. Sulfonated rayon fabric (with CI Reactive Blue 21 dye as the binding substance) prepared according to Example 2 had a 0.37 log reduction in pathogenic virus as compared to the non-sulfated rayon control fabric.

The lower limit of detection in the assay system was 3.13 logs, so that the minimum reduction in HSV titer for sulfonated rayon fabric (with CI Reactive Blue 21 dye as the binding substance) and treated with copper sulfate and zinc acetate was 4.47 logs. Thus, a minimum of 2.47 logs further viral inactivation or trapping was achieved with sulfonation and divalent metal ions versus non-sulfated, non-sulfonated rayon fabric incorporating the same amount of divalent metal ions. These results demonstrate an unexpected synergy with respect to anti-human pathogen activity between sulfonation of a fabric and the incorporation of divalent metal salts into the fabric.

According to one embodiment of the present invention, sulfated rayon fabric having a degree of sulfation (DS) of either 0.1 or 0.2 made according to Example 1, sulfated rayon fabric having a degree of sulfation (DS) of 0.2 and comprising the divalent metal salts copper sulfate and zinc acetate made according to Example 4, sulfonated rayon fabric (with CI Reactive Blue 21 dye as the binding substance) made according to Example 2, and sulfonated rayon fabric (with CI Reactive Blue 21 dye as the binding substance) and comprising the divalent metal salts copper sulfate and zinc acetate made according to Example 3, as well as to a non-sulfated, non-sulfonated rayon control fabric, and rayon fabric comprising the divalent metal salts copper sulfate and zinc acetate were assessed for their antiviral properties. 4.70 logs of influenza A virus was applied in an aerosol to a 5 cm by 5 cm area of the test fabrics and three samples of each of the test fabrics with the applied influenza A virus were allowed to sit after virus application for either 1, 5, or 15 minutes, and then placed in individual 20 ml aliquots of extraction medium and subjected to gentle agitation for 5 minutes. Serial dilutions of extraction buffers were administered into embryonated eggs for assay of pathogenic influenza A viral titer by embryonic viability and by a hemagglutinin assay of allantoic fluid from such eggs.

The results of the testing were that the sulfated rayon fabric made according to Example 1 having a degree of sulfation (DS) of either 0.1 or 0.2, both yielded no detectable pathogenic virus at each of the time points tested (1, 5 and 15 minutes), indicating an influenza virus log reduction greater than 3 at each of the time points tested compared to the amount of virus applied to the fabric. Similarly, sulfated rayon fabric made according to Example 1 having a degree of sulfation (DS) of 0.2 and comprising the divalent metal salts copper sulfate and zinc acetate also yielded no detectable pathogenic virus at each of the time points tested (1, 5 and 15 minutes), indicating an influenza virus log reduction greater than 3 at each of the time points tested compared to the amount of virus applied to the fabric.

Sulfonated rayon fabric (with CI Reactive Blue 21 dye as the binding substance), made according to Example 2, reduced influenza A virus in log reductions of 1.95 at a 1 minute test time, 2.33 at a 5 minute test time, and 3.08 at 15 minute test time. Sulfonated rayon fabric (with CI Reactive Blue 21 dye as the binding substance) and comprising the divalent metal salts copper sulfate and zinc acetate made according to Example 3, yielded no detectable pathogenic virus at each of the time points tested (1, 5 and 15 minutes), indicating an influenza virus log reduction greater than 3 at each of the time points tested.

In a preferred embodiment, the facial mask 100 comprises a fabric 200 according to the present invention, where the fabric 200 comprises a binding substance 202 according to the present invention. In a preferred embodiment, the fabric 200 further comprises one or more than one additional substance according to the present invention, other than the binding substance, that decreases the pathogenic capacity of one or more than one human pathogen. In a preferred embodiment, the one or more than one additional substance is a multivalent metallic ion, such as for example a multivalent metallic ion selected from the group consisting of multivalent copper, multivalent silver and multivalent zinc. In another embodiment, the one or more than one substance is a metallic salt, such as for example a metallic salt selected from the group consisting of copper acetate, copper oxide, copper sulfate and zinc acetate. In a particularly preferred embodiment, the metallic salt is a divalent salt. In a particularly preferred embodiment, the facial mask 100 comprises a fabric 200 comprising CI Reactive Blue 21 dye as the binding substance 202, and the fabric 200 further comprises multivalent copper and multivalent zinc.

According to another embodiment of the present invention, there is provided a method of making a facial mask 100 according to the present invention for use in decreasing the transmission of one or more than one human pathogen, including viruses that cause human respiratory tract infections. In one embodiment, facial mask 100 comprises a body 102, a flap 104, and one or more than one extension 146 attached to the body 102 for securing the facial mask 100 to the face 306 of a wearer. In one embodiment, the method comprises enclosing or surrounding a fabric 200 as disclosed in this disclosure with one or more than one heat-moldable fabric as disclosed in this disclosure. Such heat-moldable fabrics permit shaping of masks with heat or ultrasonic welding of the facial mask 100.

In one embodiment, the method comprises, first, providing a fabric 200 as disclosed in this disclosure. In a preferred embodiment, the fabric 200 further comprises one or more than one additional substance according to the present invention, other than the binding substance 202, that decreases the pathogenic capacity of one or more than one human pathogen. In a preferred embodiment, the one or more than one additional substance is a multivalent metallic ion, such as for example multivalent copper, multivalent silver or multivalent zinc, such as divalent copper or divalent zinc. In another embodiment, the one or more than one substance is a metallic salt, such as for example copper oxide, zinc acetate, copper acetate or copper sulfate. In a particularly preferred embodiment, the metallic salt is a divalent metallic salt, such as one or more than one divalent metallic salt selected from the group consisting of a salt of divalent copper and a salt of divalent zinc.

In one embodiment, the fabric 200 is cut and formed to the shape of the facial mask 100, and the one or more than one extension 146 is attached to the body 102 of the facial mask 100.

In another embodiment, the body 102 and flap 104 of the facial mask 100 comprise a material comprising a plurality of layers, such as the material 204 disclosed in this disclosure. In a particularly preferred embodiment, the plurality of layers is three layers, such as the material 204 shown in FIG. 11. In another particularly preferred embodiment, the plurality of layers is four layers, such as the material 204 shown in FIG. 12. When the facial mask comprises a material 204 according to the present invention, the method comprises providing a fabric 200 according to the present invention to form one or more than one layer of the material 204.

In one embodiment, the fabric 200 or the material 204 or both the fabric 200 and the material 204 are provided on rolls of a first size, and the rolls are cut to a second size for making the facial mask 100.

Next, the method comprises cutting the fabric 200, or cutting the layers of the material 204, into the shape of the body 102 and the flap 104.

In one embodiment, the facial mask 100 comprises a material 204 comprising a plurality of layers, and the method comprises assembling the layers of material 204 in the order of the layers, and joining the layers together. In one embodiment, the layers of the material 204 are joined together by an adhesive to create the perimeter 112 of the body 102 and the perimeter 128 of the flap 104. In a preferred embodiment, the layers of the material 204 are joined together by ultrasonic welding to create the perimeter 112 of the body 102 and the perimeter 128 of the flap 104.

In one embodiment, the method further comprises labeling the facial mask 100 with text or graphics or both text and graphics identifying the origin or content of the facial mask 100, or providing instructions on wearing the facial mask 100.

Figure 8:
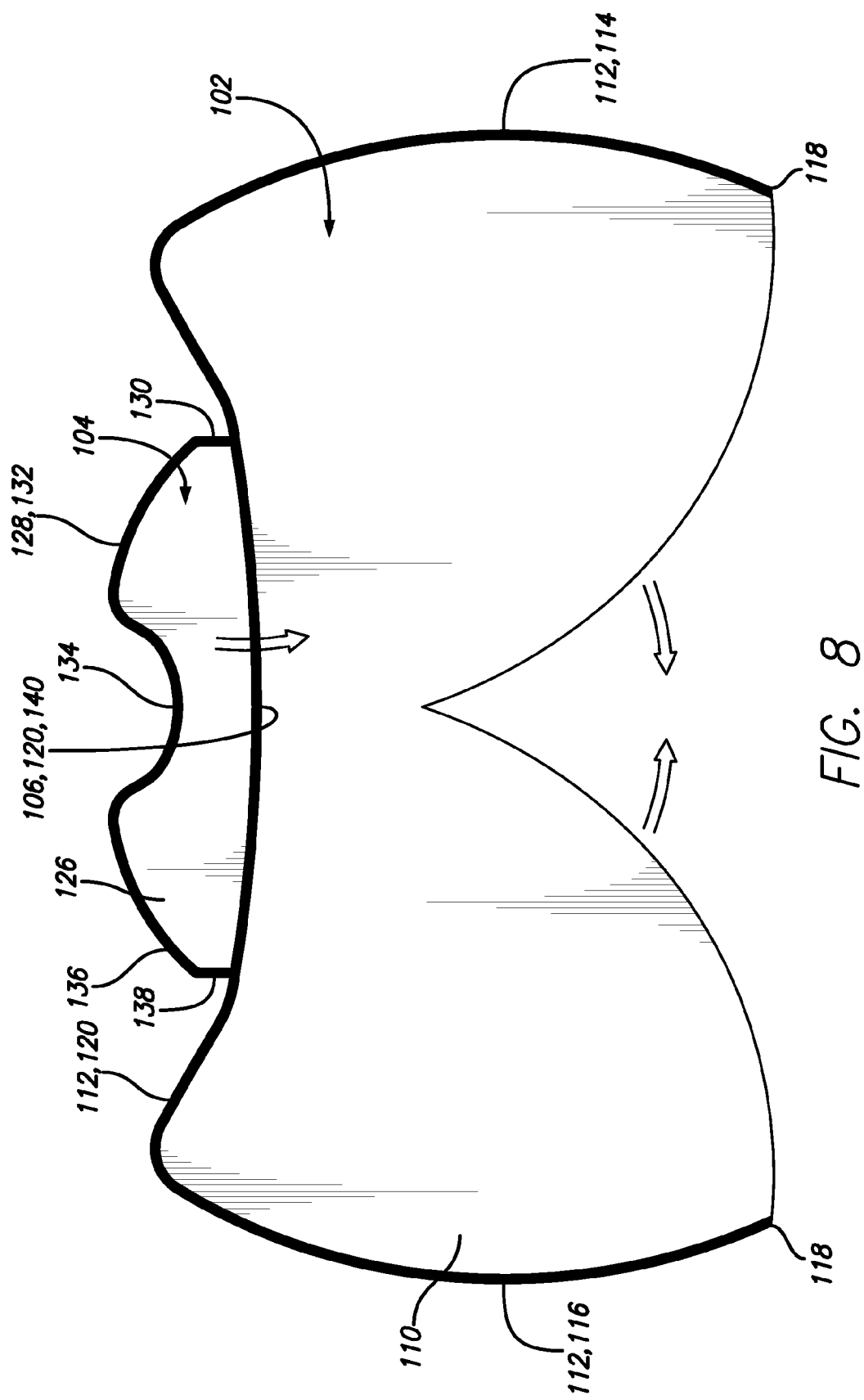
FIG. 8 is a back perspective view of part of the facial mask shown in FIG. 3 before final assembly.
Figure 9:
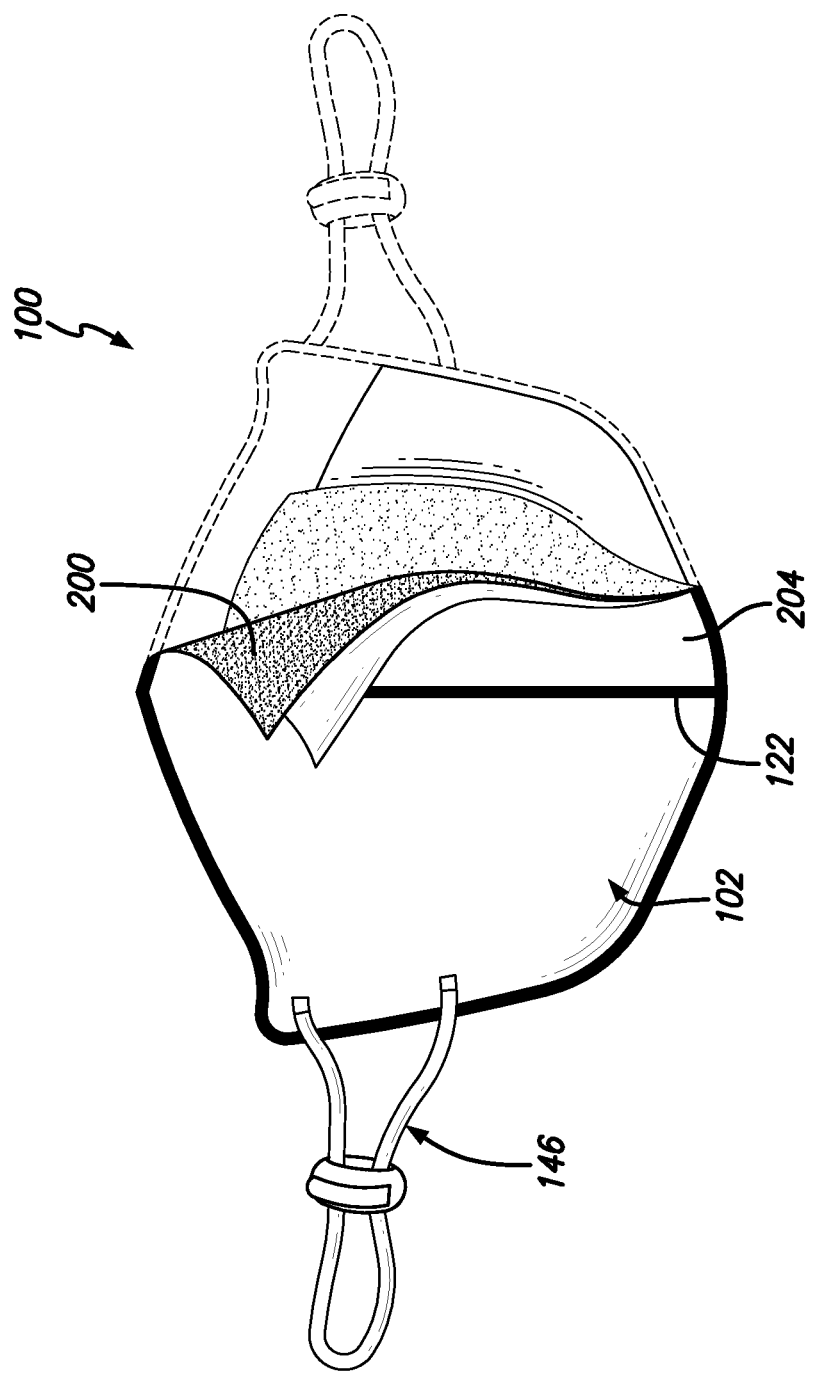
FIG. 9 is a partial, cutaway, frontal perspective view of the facial mask shown in FIG. 3 showing the multiple layers of the body of the facial mask.

In one embodiment, as can be seen in FIG. 8, at this stage, the body 102 and the flap 104 comprise the shape as shown, and the method further comprises creating a central seam 122 of the body 102 by any suitable method as will be understood by those with skill in the art with reference to this disclosure. In one embodiment, the central seam 122 of the body 102 is created by application of an adhesive. In a preferred embodiment, the central seam 122 of the body 102 is created by ultrasonic welding.

In one embodiment, the method further comprises attaching one or more than one extension 146 to the body 102. In one embodiment, the one or more than one extension 146 is attached to the body 102 by application of an adhesive. In a preferred embodiment, the one or more than one extension 146 is attached to the body 102 by ultrasonic welding.

In one embodiment, the method further comprises attaching the resilient member 142 to the facial mask 100. In one embodiment, attaching the resilient member 142 to the facial mask 100 comprises applying an adhesive to the resilient member 142 or to the flap 104 or to both the resilient member 142 and to the flap 104, and joining the resilient member 142 to the flap 104 by applying pressure to the resilient member 142 and to the flap 104.

In one embodiment, the method further comprises attaching a deformable strip 144 to the facial mask 100. In one embodiment, attaching the deformable strip 144 to the facial mask 100 comprises applying an adhesive to the deformable strip 144 or to the body 102 or to both the deformable strip 144 and to the body 102, and joining the deformable strip 144 to the body 102 by applying pressure to the deformable strip 144 and to the body 102.

Next, as can be seen in FIG. 8, the method further comprises folding the flap 104 at the body-flap junction 106 of the facial mask 100 so that the back surface 126 of the flap 104 faces the back surface 110 of the body 102. The facial mask 100 is now ready to be worn.

According to another embodiment of the present invention, there is provided a method of decreasing the transmission of one or more than one human pathogen. In one embodiment, the method comprises providing a facial mask 100 according to the present invention, and wearing the facial mask 100.

Figure 13:
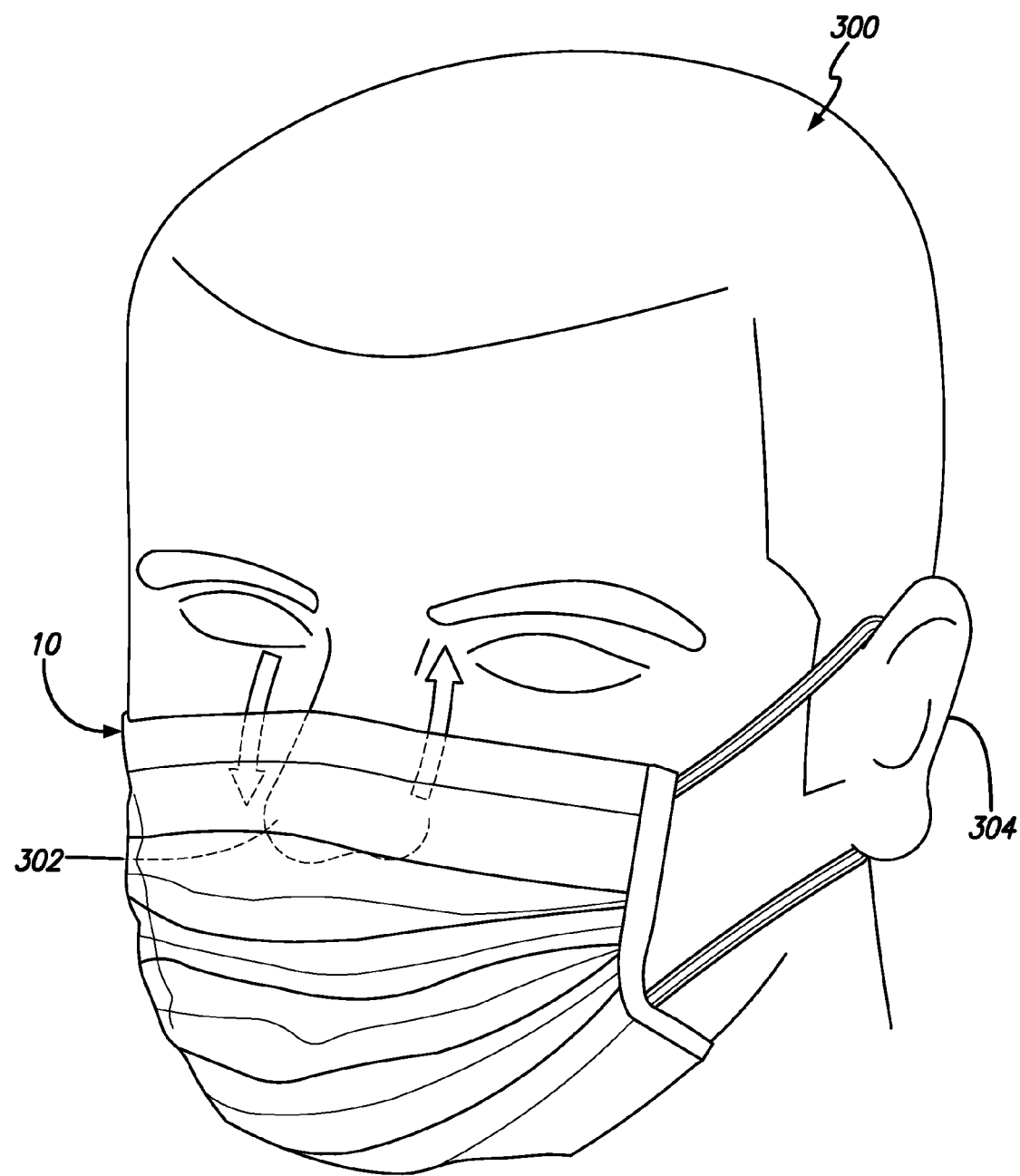
FIG. 13 is a frontal perspective view of the embodiment of the facial mask shown in FIG. 1 and FIG. 2 being worn by a wearer.

The facial mask 100 according to one embodiment of the present invention has two advantages. Referring now to FIG. 13 is a frontal perspective view of the embodiment of the facial mask shown in FIG. 1 and FIG. 2 being worn by a wearer. As can be seen, a first advantage to the facial mask 100 according to the present invention is that the flap 104 of the facial mask 100 according to the present invention confers a better fit than the conventional facial mask 10 around the nose 302 of the wearer 300, and thereby wearing the facial mask 100 according to the present invention, when compared with wearing a conventional facial mask 10, decreases egress of airborne infectious particles outward from the space between the facial mask 100 and the face 306 of the wearer 300 (shown as the up arrow), or decreases ingress of airborne infectious particles from around the perimeter 112 of the facial mask 100 into the space between the facial mask 100 and the face 306 of the wearer 300 (shown as the down arrow), or both decreases egress of airborne infectious particles outward from the space between the facial mask 100 and the face 306 of the wearer 300 (shown as the up arrow) and decreases ingress of airborne infectious particles from around the perimeter 112 of the facial mask 100 into the space between the facial mask 100 and the face 306 of the wearer 300 (shown as the down arrow). This advantage decreases the transmission of one or more than one human pathogen by preventing contagion of the wearer 300 of the facial mask 100 according to the present invention with infectious particles from a third person, and by decreasing the transmission of one or more than one human pathogen from the wearer 300 of the facial mask 100 according to the present invention to a third party.

Further as can be seen in the Figures, a second advantage to the facial mask 100 according to the present invention is folding the flap 104 over at the body-flap junction 106 toward the back surface 110 of the body 102 of the facial mask 100, inverts the layers of the material 204 of the flap 104 with respect to the layers of material 204 of the body 102. This inversion of orientation causes airborne infectious particles expelled from the wearer 300 or entering the space between the facial mask 100 and the face 306 of the wearer 300 from outside the perimeter 112 of the facial mask 100 to encounter the fabric 200, thereby binding some of the infectious particles to the fabric 200, and thereby decreasing the transmission of one or more than one human pathogen by preventing contagion of the wearer 300 of the facial mask 100 according to the present invention with infectious particles from a third person, and by decreasing the transmission of one or more than one human pathogen from the wearer 300 of the facial mask 100 according to the present invention to a third party.

According to another embodiment of the present invention, there is provided a composition for coating a polypropylene-based fabric or polypropylene-based material, such as for example a fabric or a material according to the present invention for use in decreasing the transmission of the human pathogens. In one embodiment, the composition decreases the hydrophobicity of the polypropylene-based fabric or polypropylene-based material, thereby increasing the transmission of the human pathogens through the polypropylene-based fabric or polypropylene-based material. In another embodiment, the composition has additional direct antibacterial, antifungal and antiviral activity. The composition provides a durable coating that adheres to the polypropylene-based fabric or polypropylene-based material. The composition is compatible with high-speed manufacturing processes such as the ultrasonic shaping and welding of protective face masks that comprise thermoplastic polypropylene-based fabric or polypropylene-based material. In a preferred embodiment, the composition is coated onto the surface of the polypropylene-based fabric or polypropylene-based material. In a preferred embodiment, the composition is coated onto two of the two or more than two layers of the polypropylene-based material.

In one embodiment, the composition comprises citric acid (also known as 2-hydroxypropane-1,2,3-tricarboxylic acid or 3-hydroxypentanedioic acid-3-carboxylic acid or hydrogen citrate) and comprises polyvinyl alcohol (also known as Alkotex; Alvyl; Covol; Ethenol, Gelvatol; homopolymer; Lemol; Mowiol; Poly(Ethenol), Polyviol; PVA; PVOH and Vinol). In a preferred embodiment, the polyvinyl alcohol is a partially hydrolyzed form of polyvinyl alcohol which allows the composition to optimally adhere to a polypropylene-based fabric or polypropylene-based material while also forming a durable coating when mixed with citric acid (with or without a nonionic surfactant). In one embodiment, the polyvinyl alcohol is Elvanol® 51-05 (E. I. du Pont Distal end 28 Nemours and Company Corporation, Del., Md. US).

In a preferred embodiment, the composition for coating a polypropylene-based fabric or polypropylene-based material further comprises one or more than one nonionic surfactant. The nonionic surfactant increases the antibacterial, antifungal and antiviral activity of a polypropylene-based fabric or polypropylene-based material coated with the composition both by direct actions on the pathogenic particles and by increasing the dispersion of the citric acid through the polypropylene-based fabric or polypropylene-based material upon contact of the composition treated polypropylene-based fabric or polypropylene-based material with aerosol droplets containing human pathogens. In one embodiment, the nonionic surfactant is polyoxyethylene (20) sorbitan (also known as monolaurate; polysorbate 20; PEG (20) sorbitan monolaurate; and Tween 20).

In one embodiment, the composition is an aqueous solution. In a preferred embodiment, the water portion of the aqueous solution is distilled water.

In one embodiment, the composition comprises an aqueous solution of between 0.5% to 4% citric acid and between 0.5% and 4% polyvinyl alcohol. In another embodiment, the composition comprises an aqueous solution of between 1% and 3% citric acid and between 1% and 3% polyvinyl alcohol. In a preferred embodiment, the composition comprises an aqueous solution of 2% polyvinyl alcohol and 2% citric acid. In one embodiment, the composition comprises between 0.1% and 1% of the nonionic surfactant. In another embodiment, the composition comprises between 0.2% and 0.7% of the nonionic surfactant. In a preferred embodiment, the composition comprises 0.5% of the nonionic surfactant. In a particularly preferred embodiment, the composition is an aqueous solution comprising 2% citric acid, 2% polyvinyl alcohol and 0.5% of the nonionic surfactant.

In a preferred embodiment, the composition for coating a polypropylene-based fabric or polypropylene-based material further comprises one or more than one type of bactericidal, fungicidal or viricidal agent. The bactericidal, fungicidal or viricidal agent can be any antibacterial, antifungal and antiviral agent that is physically compatible with the other components of the composition (citric acid, polyvinyl alcohol, and the nonionic surfactant). In one embodiment, the agent is a multivalent metallic ion, such as for example multivalent copper, multivalent silver or multivalent zinc, all of which are antibacterial, antifungal and antiviral. In a particularly preferred embodiment, the metallic ion is a divalent metallic salt, such as one or more than one divalent metallic salt selected from the group consisting of a salt of divalent copper and a salt of divalent zinc, such as for example divalent metallic salt selected from the group consisting of copper acetate, copper oxide, copper sulfate and zinc acetate, all of which are bactericidal, viricidal and fungicidal. In one embodiment, the composition comprises copper acetate and zinc acetate. In one embodiment, the composition comprises between 0.5% and 5% of each of the one or more than one metallic ion. In another embodiment, the composition comprises between 1% and 4% of each of the one or more than one metallic ion. In another embodiment, the composition comprises 3% of each of the one or more than one metallic ion. In one embodiment, the composition comprises 3% copper acetate and 3% zinc acetate.

Advantageously, the composition increases the hydrophilicity of polypropylene-based fabric (such as for example through spunbond non-woven polypropylene fiber (SBPF) or melt blown polypropylene fiber (MBPF)) or polypropylene-based material when the composition is dried onto the polypropylene-based fabric or polypropylene-based material. This increases permeation of liquids, allowing aerosol droplets containing human pathogens to pass through the surface of the polypropylene-based fabric or polypropylene-based material instead of remaining on the surface of the polypropylene-based fabric or polypropylene-based material so that the aerosol droplets containing human pathogens encounter another layer that decreases the transmission of the human pathogen by antibacterial, antifungal and antiviral activity, such as for example a layer of fabric according to the present invention that decreases the transmission of the human pathogen by antibacterial, antifungal and antiviral activity comprising a reactive dye or comprising one or more than one divalent metallic salt. The acidic nature of the citric acid component of the composition acts as a hydrophilic plasticizing agent for the polyvinyl alcohol, and also provides an acidic environment that contributes to the total antibacterial, antifungal and antiviral activity of the fabric.

Additionally, the composition advantageously does not obstruct airflow, making the composition suitable for use on polypropylene-based fabrics and polypropylene-based materials used as part of a protective face mask.

The composition of the present invention can be made by any suitable process, as will be understood by those with skill in the art with reference to this disclosure. For example, in one embodiment, the composition is an aqueous solution comprising 2% citric acid, 2% polyvinyl alcohol and 0.5% polyoxyethylene (20) sorbitan, and the composition is made by dissolving the citric acid, polyvinyl alcohol and polyoxyethylene (20) sorbitan in distilled water, boiling the solution at 80° C. until the polyvinyl alcohol is completely dissolved, and then allowing the solution to cool down to room temperature before use. In another example, the composition is an aqueous solution comprising 2% citric acid, 2% polyvinyl alcohol, 0.5% polyoxyethylene (20) sorbitan, 3% copper acetate and 3% zinc acetate, and the composition is made by dissolving sufficient copper acetate powder and zinc acetate powder into the solution made according to the preceding example.

The composition is applied to a polypropylene-based fabric or polypropylene-based material by any suitable method as will be understood by those with skill in the art with reference to this disclosure, such as for example by dipping the polypropylene-based fabric or polypropylene-based material into the composition, or by spraying or rolling the composition onto the polypropylene-based fabric or polypropylene-based material, and then drying the polypropylene-based fabric or polypropylene-based material. In one embodiment, drying comprises allowing the composition coated polypropylene-based fabric or composition coated polypropylene-based material to air dry at room temperature. In another embodiment, drying comprises using forced air or heat, such as for example by contacting the composition coated polypropylene-based fabric or composition coated polypropylene-based material with a heated roller in a production line.

As will be understood by those with skill in the art with reference to this disclosure, coating a polypropylene-based fabric or polypropylene-based material with the composition can be accomplished using a continuous production process where rolls of polypropylene-based fabric or polypropylene-based material are coated with the composition and dried, and then the coated polypropylene-based fabric or polypropylene-based material can be fed directly into fabrication machinery for producing a final structure, such as for example a protective face mask, or can be stored for later use.

As will be understood by those with skill in the art with reference to this disclosure, the composition can be used on any polypropylene-based fabric or polypropylene-based material, such as for example a polypropylene-based fabric or polypropylene-based material incorporated into a protective face mask. In one embodiment, there is provided a composition coated polypropylene-based material having alternating spunbond non-woven polypropylene fiber (S) and melt blown polypropylene fiber (M) layers, such as for example MS, SM, SMS, SSMS, SMSS, SMSMS, SMMSS and SSMMS. In one embodiment, the polypropylene-based material having alternating spunbond non-woven polypropylene fiber (S) and melt blown polypropylene fiber (M) layers further comprises one or more than one layer that decreases the transmission of the human pathogen by antibacterial, antifungal and antiviral activity, such as for example, a layer of fabric according to the present invention that decreases the transmission of the human pathogen by antibacterial, antifungal and antiviral activity. In one embodiment, the polypropylene-based material having the alternating layers is incorporated into a protective face mask.

The antiviral effectiveness of a composition according to the present invention for coating a polypropylene-based fabric or polypropylene-based material was tested using four types of material, where each type of material had four layers in the following order:

Layer #1: spunbond non-woven polypropylene fiber (SBPF);
Layer #2: rayon;

Layer #3: melt blown polypropylene fiber (MBPF); and
Layer #4: spunbond non-woven polypropylene fiber (SBPF).

The four types of materials were:
Material #1: (the control) no composition coating on Layer #1; no binding substance in Layer #2;
Material #2: no composition coating on Layer #1; Layer #2 comprising Reactive Blue 21 dye, copper acetate and zinc acetate according to the present invention;
Material #3: Layer #1 dipped in an aqueous composition comprising 2% polyvinyl alcohol and 2% citric acid according to the present invention, then drained and air-dried; Layer #2 comprising Reactive Blue 21 dye, copper acetate and zinc acetate according to the present invention; and
Material #4: Layer #1 dipped in an aqueous composition comprising 2% citric acid, 2% polyvinyl alcohol and 0.5% polyoxyethylene (20) sorbitan according to the present invention, then drained and air-dried; Layer #2 comprising Reactive Blue 21 dye, copper acetate and zinc acetate according to the present invention.

Each of the four materials were tested for antiviral activity by misting 9.6 logs of live Influenza A (H1N1) virus onto 5 cm by 5 cm squares of the material in a volume of 0.4 ml of buffered saline. After exposure times of 1 minute or 5 minutes, each material was transferred to a cell culture medium for extraction of residual live virus, which was then quantified by infectivity in a test cell line according to techniques known to those with skill in the art.

Referring now to Table 2, as can be seen, Material #1 (the control) did not reduce viral load at either the contact times of 1 and 5 minutes. Material #2, comprising a material according to the present invention reduced viral load by 2 and 2.5 logs at 1 minute and 5 minutes, respectively. Material #3, which was identical to Material #2 except that layer #1 was coated with a composition according to the present invention comprising 2% citric acid and 2% polyvinyl alcohol, reduced viral load by 4.25 logs at both 1 minute and 5 minutes, respectively. Material #4 which was identical to Material #2 except that layer #1 was coated with a composition according to the present invention comprising 2% citric acid, 2% polyvinyl alcohol and 0.5% polyoxyethylene (20) sorbitan reduced viral load by 5.5 and 6 logs at 1 minute and 5 minutes, respectively.

TABLE 2

RESULTS OF ASSESSMENT OF MATERIAL FOR ANTIVIRAL PROPERTIES

| MATERIAL TESTED | Time | Input Load (Log$_{10}$ TCID$_{50}$) | Output Load (Log$_{10}$ TCID$_{50}$) | LOG$_{10}$ Reduction |
|---|---|---|---|---|
| liquid control | 1 minute | | 9.60 ± 0.28 | N/A |
| | 5 minute | | 9.60 ± 0.28 | N/A |
| Material #1 | 1 minute | 9.60 ± 0.28 | 9.60 ± 0.28 | — |
| | 5 minute | 9.60 ± 0.28 | 9.60 ± 0.28 | — |
| Material #2 | 1 minute | 9.60 ± 0.28 | 7.60 ± 0.28 | 2.00 ± 0.40 |
| | 5 minute | 9.60 ± 0.28 | 7.10 ± 0.00 | 2.50 ± 0.28 |
| Material #3 | 1 minute | 9.60 ± 0.28 | 5.35 ± 0.25 | 4.25 ± 0.38 |
| | 5 minute | 9.60 ± 0.28 | 5.35 ± 0.25 | 4.25 ± 0.38 |
| Material #4 | 1 minute | 9.60 ± 0.28 | 4.10 ± 0.35 | 5.50 ± 0.45 |
| | 5 minute | 9.60 ± 0.28 | 3.60 ± 0.28 | 6.00 ± 0.40 |

Therefore, as can be appreciated from these data, coating a polypropylene-based fabric or polypropylene-based material with a composition according to the present invention results in a substantial increase in antiviral activity of the material.

Further, the effect of increasing the hydrophilicity of the polypropylene-based fabric by coating the polypropylene-based fabric with a composition according to the present invention was demonstrated by comparing the rate of absorption of aqueous droplets applied to Layer #1 (a spunbond polypropylene layer) of samples of Material #2 and Material #4. As indicated above, Material #2 and Material #4 were identical except that Material #4 had a coating of the composition comprising 2% citric acid, 2% polyvinyl alcohol and 0.5% polyoxyethylene (20) sorbitan to Layer #1. A droplet of distilled water (1 microliter) was dropped onto the surface of Layer #1 of Material #2 and Layer #1 of Material #4. The process of absorption was documented with a CCD (charge-coupled device) camera attached to a microscope, capturing images every 10 minutes for Material #2 and every 5 seconds for Material #4, and also capturing additional images at the time of complete droplet absorption. The results of these tests showed that the time required for complete absorption of a 1 microliter droplet of water into Material #2, without a hydrophilic coating on the outer polypropylene layer, was 42 minutes, and into Material #2 within 22 seconds. Therefore, coating Material #4 with the composition resulted in absorption of water approximately 100 times faster than without the composition.

The antiviral effectiveness of another composition according to the present invention for coating a polypropylene-based fabric or polypropylene-based material was tested using the following three types of fabrics and two, four-layered type of material as follows:
Fabric #1: (the control) nonwoven polypropylene fabric (45 g/m$^2$) with no composition coating;
Fabric #2: nonwoven polypropylene fabric (45 g/m$^2$) coated with a composition according to the present invention comprising 2% citric acid, 2% polyvinyl alcohol and 0.5% polyoxyethylene (20) sorbitan;
Fabric #3: nonwoven polypropylene fabric (45 g/m$^2$) coated with a composition according to the present invention comprising 2% citric acid, 2% polyvinyl alcohol, 0.5% polyoxyethylene (20) sorbitan, 2% copper acetate and 2% zinc acetate;
Material #4: four-layered material comprising Layer #1: spunbond non-woven polypropylene fiber (SBPF); Layer #2: nonwoven polypropylene fabric (45 g/m$^2$) coated with a composition according to the present invention comprising 2% citric acid, 2% polyvinyl alcohol and 0.5% polyoxyethylene (20) sorbitan; Layer #3: melt blown polypropylene fiber (MBPF); and Layer #4: spunbond non-woven polypropylene fiber (SBPF); and
Material #5: four-layered material comprising Layer #1: spunbond non-woven polypropylene fiber (SBPF); Layer #2: rayon treated with a composition of Reactive Blue 21 dye, copper acetate and zinc acetate according to the present invention; Layer #3: melt blown polypropylene fiber (MBPF); and Layer #4: spunbond non-woven polypropylene fiber (SBPF).

Each of the three fabrics and two materials were tested for antiviral activity by misting 6.35 logs of live Influenza B (B/Lee/40) virus onto 5 cm by 5 cm squares of the fabrics and material in a volume of 0.4 ml of buffered saline. After an exposure time of 5 minutes, each fabric and material was transferred to cell culture medium for extraction of residual live virus, which was then quantified by infectivity in a test cell line according to techniques known to those with skill in the art.

Referring now to Table 3, as can be seen, coating a polypropylene-based fabric or polypropylene-based material with different compositions according to the present invention as indicated resulted in a comparable antiviral activity.

TABLE 3

RESULTS OF ASSESSMENT OF FABRIC AND MATERIAL FOR ANTIVIRAL PROPERTIES

| | Time | Input Load ($Log_{10}$ $TCID_{50}$) | Output Load ($Log_{10}$ $TCID_{50}$) | $LOG_{10}$ Reduction |
|---|---|---|---|---|
| Liquid Control | | | 6.35 ± 0.37 | N/A |
| Fabric #1 (control) | 5 minutes | 6.35 ± 0.37 | 6.35 ± 0.37 | 0 |
| Fabric #2 | 5 minutes | 6.35 ± 0.37 | Not detectable | >4 |
| Fabric #3 | 5 minutes | 6.35 ± 0.37 | Not detectable | >4 |
| Material #1 | 5 minutes | 6.35 ± 0.37 | Not detectable | >4 |
| Material #2 | 5 minutes | 6.35 ± 0.37 | Not detectable | >4 |

According to one embodiment of the present invention, there is provided a polypropylene-based fabric or polypropylene based material comprising a composition on either one surface or two surfaces. According to another embodiment of the present invention, there is provided a device that decreases the transmission of one or more than one human pathogen by antibacterial, antifungal and antiviral activity, where the device comprises a polypropylene-based fabric or polypropylene-based material coated with a composition according to the present invention. According to another embodiment of the present invention, there is provided a method of decreasing the transmission of one or more than one human pathogen, where the method comprises providing a device comprising a polypropylene-based fabric or polypropylene-based material coated with a composition according to the present invention, and using the device. In one embodiment, the device is a facial mask according to the present invention. In a particularly preferred embodiment, the device is a facial mask according to the present invention, where the body (and the flap when present) of the facial mask comprises four layers oriented from front to back, where Layer #1 comprises spunbond nonwoven polypropylene fiber having a density of 45 g/m² and coated with a composition according to the present invention comprising 2% citric acid, 2% polyvinyl alcohol and 0.5% polyoxyethylene (20) sorbitan, Layer #2 comprises spunbond nonwoven polypropylene fiber having a density of 45 g/m² and coated with a composition according to the present invention comprising 2% citric acid, 2% polyvinyl alcohol, 0.5% polyoxyethylene (20) sorbitan, 3% copper acetate and 3% zinc acetate, Layer #3 comprises melt-blown polypropylene fiber having a density of 18 g/m², and Layer #4 comprises spunbond nonwoven polypropylene fiber having a density of 25 g/m².

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A facial mask that decreases the transmission of one or more than one human pathogen by antibacterial, antifungal and antiviral activity, the facial mask comprising a wearable facial mask configured for placement over a mouth and nose, the wearable facial mask having a polypropylene-based material comprising four layers, Layer #1, Layer #2, Layer #3 and Layer #4 oriented from a front surface of the facial mask to a back surface of the facial mask, wherein the back surface of the facial mask is a surface of Layer #4 contacting the face of a wearer, and the front surface of the facial mask opposing to the back surface of the facial mask; wherein Layer #1 is a spunbond nonwoven fabric comprising polypropylene fibers having a density of 45 g/m² and having a Layer #1 coating prepared from drying a Layer #1 wet coating formed by coating Layer #1 with a Layer #1 aqueous coating composition comprising 2% by weight of citric acid, 2% by weight of polyvinyl alcohol, and 0.5% by weight of polyoxyethylene (20) sorbitan by the total weight of the Layer #1 aqueous coating composition, Layer #2 is a spunbond nonwoven fabric comprising polypropylene fibers having a density of 45 g/m² and having a Layer #2 coating prepared from drying a Layer #2 wet coating formed by coating Layer #2 with a Layer #2 aqueous coating composition comprising 3% by weight of copper acetate and 3% by weight of zinc acetate by the total weight of the Layer #2 aqueous coating composition, Layer #3 is a melt-blown polypropylene fabric comprising polypropylene fibers having a density of 18 g/m², and Layer #4 is a spunbond nonwoven polypropylene fabric comprising polypropylene fibers having a density of 25 g/m².

2. A facial mask for decreasing the transmission of one or more than one human pathogen to and from a human wearer of the facial mask, the facial mask comprising: a) a body comprising a front surface of the body, an opposing back surface of the body, and a perimeter of the body defining a shape of the body, and a central seam, wherein the back surface the body contacting the face of the human wearer and the front surface of the body opposing to the back surface of the body; b) a flap attached to the body at a body-flap junction; the flap comprising a front surface of the flap, an opposing back surface of the flap, and a perimeter of the flap defining a shape of the flap; c) a resilient member attached to the back surface of the flap; d) a deformable strip attached to the body; and e) one or more than one extension attached to the body for securing the facial mask to the head of a wearer; where the perimeter of the body comprises a right lateral edge, a left lateral edge connected to the right lateral edge at a bottom junction of the perimeter, and a top edge connecting the right lateral edge to the left lateral edge; where the perimeter of the flap comprises in continuity, a right vertical side, a right arcuate side, a central curved region, a left arcuate side, a left vertical side, and a base partially forming the body-flap junction and connecting the right vertical side to the left vertical side; where the shape of the flap is an inverted U-shape when looking at the front surface of the body or the back surface of the body with the bottom junction oriented down; where both the body and the flap comprise a material comprising four layers, Layer #1, Layer #2, Layer #3 and Layer #4 oriented from the front surface to the back surface, wherein the back surface is a back surface of Layer #4; and where Layer #1 is a spunbond nonwoven fabric comprising polypropylene fibers having a density of 45 g/m² and having a Layer #1 coating prepared from drying a Layer #1 wet coating formed by coating Layer #1 with a Layer #1 aqueous coating composition comprising 2% by weight of citric acid, 2% by weight of polyvinyl alcohol, and 0.5% by weight of polyoxyethylene (20) sorbitan by the total weight of the Layer #1 aqueous coating composition, Layer #2 is a spunbond nonwoven fabric comprising polypropylene fibers having a density of 45 g/m² and having a Layer #2 coating prepared from drying a Layer #2 wet coating formed by coating Layer #2 with a Layer #2 aqueous coating composition comprising 3% by weight of copper acetate and 3% by weight zinc acetate by the total weight of the Layer #2 aqueous coating composition, Layer #3 is a melt-blown polypropylene fabric comprising polypropylene fibers having a density of 18 g/m², and Layer #4 is a spunbond nonwoven polypropylene fabric comprising polypropylene fibers having a density of 25 g/m².

3. The facial mask of claim 1, further comprising one or more than one reactive dye.

4. The facial mask of claim 2, further comprising one or more than one reactive dye.

5. The facial mask of claim 1, wherein the Layer #2 aqueous coating composition further comprises 2% by weight of citric acid, 2% by weight of polyvinyl alcohol, and 0.5% by weight of polyoxyethylene (20) sorbitan by the total weight of the Layer #2 aqueous coating composition.

6. The facial mask of claim 2, wherein the Layer #2 aqueous coating composition further comprises 2% by weight of citric acid, 2% by weight of polyvinyl alcohol, and 0.5% by weight of polyoxyethylene (20) sorbitan by the total weight of the Layer #2 aqueous coating composition.

* * * * *